United States Patent
Li

(10) Patent No.: US 11,376,205 B2
(45) Date of Patent: Jul. 5, 2022

(54) WATER-IN-OIL EMULSION CONTAINING BAICALIN, A XANTHINE BASE, A VITAMIN B3, AND A POLYVALENT METAL CATION SALT

(71) Applicant: L'OREAL, Paris (FR)

(72) Inventor: Hong Li, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/470,850

(22) PCT Filed: Nov. 24, 2017

(86) PCT No.: PCT/EP2017/080310
§ 371 (c)(1),
(2) Date: Jun. 18, 2019

(87) PCT Pub. No.: WO2018/114213
PCT Pub. Date: Jun. 28, 2018

(65) Prior Publication Data
US 2019/0374455 A1  Dec. 12, 2019

(30) Foreign Application Priority Data

Dec. 21, 2016  (FR) ..................... 1662977

(51) Int. Cl.
*A61K 8/60* (2006.01)
*A61K 8/9789* (2017.01)
*A61K 8/06* (2006.01)
*A61K 8/49* (2006.01)
*A61Q 1/12* (2006.01)

(52) U.S. Cl.
CPC .............. *A61K 8/602* (2013.01); *A61K 8/064* (2013.01); *A61K 8/4926* (2013.01); *A61K 8/4953* (2013.01); *A61K 8/9789* (2017.08); *A61Q 1/12* (2013.01)

(58) Field of Classification Search
None
See application file for complete search history.

(56) References Cited

U.S. PATENT DOCUMENTS 5,879,668 A  *  3/1999  Hanna ..................... A61K 8/06
                                                             424/401
6,338,855 B1 *  1/2002  Albacarys ............ A61K 8/0208
                                                             424/402
2015/0005247 A1   1/2015  Chen et al.

FOREIGN PATENT DOCUMENTS

WO  WO 2014/059228 A1  4/2014
WO  WO 2015/002872 A1  1/2015

OTHER PUBLICATIONS

International Search Report dated Jan. 10, 2018, in PCT/EP2017/080310 filed on Nov. 24, 2017.
Database GNPD (Online) Mintel, "Cellular Energy Day Cream", Jun. 30, 2010, XP002771477, Database Accession No. 1354750, total 4 pages.
Office Action as received in the corresponding CN Patent Application 201780078737.7 w/partial English Translation, dated Aug. 16, 2021, 10 pages.
Cellular Energy Day Cream, Database GNPD, accession No. 1354750 /http:/www.gnpd.com.

* cited by examiner

*Primary Examiner* — Jessica Worsham
(74) *Attorney, Agent, or Firm* — Oblon, McClelland, Maier & Neustadt, L.L.P.

(57) ABSTRACT

The invention provides, in the field of caring for and/or making up keratin materials, especially the skin, a composition in water-in-oil emulsion form, containing:
a) a continuous oily phase,
b) a discontinuous aqueous phase dispersed in the oily phase;
c) at least baicalin and/or a derivative thereof and/or a plant extract containing the compound(s);
d) at least one vitamin B3 and/or a derivative thereof;
e) at least one xanthine base and/or a plant extract containing same; and
f) at least one polyvalent cation salt.

17 Claims, No Drawings

WATER-IN-OIL EMULSION CONTAINING BAICALIN, A XANTHINE BASE, A VITAMIN B3, AND A POLYVALENT METAL CATION SALT

The present invention aims to propose, for the field of caring for and/or making up keratin materials, especially the skin, a novel composition in the form of a water-in-oil emulsion, containing at least:

a) a continuous oily phase, and
b) a discontinuous aqueous phase dispersed in said oily phase;
c) at least baicalin and/or a derivative thereof, in particular of general formula (I) as defined in detail below; and
d) at least one vitamin B3 and/or a derivative thereof; and
e) at least one xanthine base and/or a plant extract containing same; and
f) at least one polyvalent cation salt.

The invention also relates to a process for caring for and/or making up keratin materials, such as the skin, characterized in that it comprises the application to the keratin materials of a composition as defined previously.

Numerous cosmetic compositions for caring for and/or making up keratin materials such as the skin have been proposed with baicalin or an extract containing same, especially a scullcap root extract: *Scutellaria*, and in particular *Scutellaria baicalensis*, with the INCI name: *SCUTELLARIA BAICALENSIS* ROOT EXTRACT. Baicalin, of following formula (II)

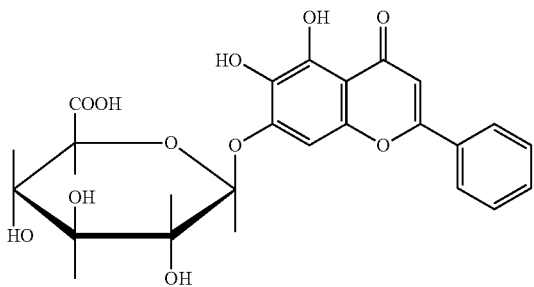

(II)

is a particularly beneficial polyphenol in cosmetics due to its antioxidant activity which makes it possible to treat or prevent the premature ageing of keratin materials such as the skin, induced by UV radiation or atmospheric agents such as pollutants. However, the solubility of baicalin is very low in aqueous medium. It is therefore very difficult to incorporate into an aqueous composition, in particular a cosmetic composition, at high levels, at which it tends to recrystallize.

It has already been proposed in applications WO14059228, U.S. Pat. Nos. 9,107,853, 9,072,919 and WO15002872 to use hydrotropic agents, in particular chosen from a vitamin B3, caffeine and mixtures thereof, in aqueous formulations to improve the solubility of the baicalin. However, the emulsions of water-in-oil type proposed in these documents generally contain monovalent alkali metal salts such as sodium chloride or sodium citrate.

During their research, the applicant observed that these water-in-oil emulsions did not have a fully satisfactory storage stability at low temperatures (i.e.: 4° C.), which may be reflected in the observation of a white smear on the surface of the composition.

Water-in-oil emulsions are highly sought-after galenical forms, due to the ease with which they are applied to the skin and their sensory properties in cosmetics in the care field, especially in sun compositions, anti-ageing compositions and in makeup, such as foundation.

The aim of the present invention is therefore to find novel water-in-oil emulsions combining baicalin and/or a derivative thereof with at least one suitable hydrotrope, which have good storage stability at low temperatures (i.e.: 4° C.), at room temperature (i.e.: 25° C.) and at high temperatures (i.e.: 45° C.) without the abovementioned drawbacks, namely the problems of stability of the composition, of solubility and of recrystallization of these active agents in the aqueous phase.

The applicant has discovered, surprisingly, that this objective could be achieved with a composition, especially comprising a physiologically acceptable medium, especially for making up and/or caring for keratin materials, in the form of a water-in-oil emulsion, containing at least:

a) a continuous oily phase, and
b) a discontinuous aqueous phase dispersed in said oily phase;
c) at least baicalin and/or a derivative thereof, in particular of general formula (I) as defined in detail below, and/or a plant extract containing said compound(s); and
d) at least one vitamin B3 and/or a derivative thereof; and
e) at least one xanthine base and/or a plant extract containing same; and
f) at least one polyvalent metal cation salt.

This discovery forms the basis of the invention.

Thus, according to one aspect thereof, the present invention relates to a composition, especially comprising a physiologically acceptable medium, especially for making up and/or caring for keratin materials, in the form of a water-in-oil emulsion, containing at least:

a) a continuous oily phase, and
b) a discontinuous aqueous phase dispersed in said oily phase;
c) at least baicalin and/or a derivative thereof, in particular of general formula (I) as defined in detail below, and/or a plant extract containing said compound(s); and
d) at least one vitamin B3 or a derivative thereof; and
e) at least one xanthine base and/or a plant extract containing same; and
f) at least one polyvalent cation salt.

The invention also relates to a process for caring for and/or making up keratin materials, such as the skin, characterized in that it comprises the application to the keratin materials of a composition as defined previously.

Definitions

Within the context of the present invention, "keratin material" means the skin, the lips, the eyelashes, the eyebrows, the head hair, the body hair and the nails, and more particularly the skin (body, face, area around the eyes, eyelids).

The term "physiologically acceptable" means compatible with the skin and/or its integuments, which has a pleasant colour, odour and feel, and which does not cause any unacceptable discomfort (stinging, tautness or redness) liable to discourage the consumer from using this composition.

For the purposes of the present invention, "water-in-oil emulsion", also referred to as inverse emulsion, is intended to denote any composition constituted of a continuous oily phase in which the aqueous phase is dispersed in the form of droplets so as to observe a macroscopically homogeneous mixture with the naked eye.

The term "polyvalent metal cation" means any ion chosen from alkaline earth metals or transition metals comprising at least two positive electric charges and having a valency of at least 2 and preferably 2 or 3.

Baicalin and Derivatives Thereof

The compositions according to the invention comprise at least baicalin and/or a derivative thereof and/or a plant extract containing said compound(s).

Baicalin and derivatives thereof have been described, as have the processes for the preparation thereof, especially, in application WO2005044281, those corresponding to the following general formula (I):

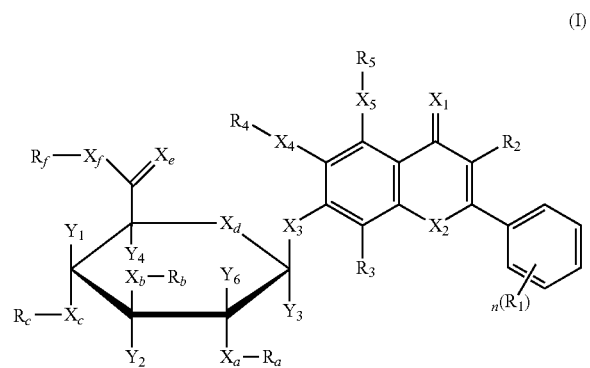

wherein each $X_1$, $X_2$, $X_3$, $X_4$, $X_5$, $X_a$, $X_b$, $X_c$, $X_d$, $X_e$ and $X_f$, independently denotes O or S;

each $Y_1$, $Y_2$, $Y_3$, $Y_4$, $Y_6$, independently denotes H or a $(C_1$-$C_{10})$alkyl radical, in particular methyl;

each $R_4$, $R_5$, $R_a$, $R_b$ et $R_c$, independently denotes H, a $(C_1$-$C_{10})$alkyl radical optionally substituted by 1 to 5 groups $R_y$, or a $(C_1$-$C_{10})$alkyl-O—$(C_1$-$C_{10})$alkyl radical, each $(C_1$-$C_{10})$alkyl radical possibly being substituted by 1 to 5 groups $R_y$;

each $R_y$, independently denotes $R_q$ or a —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$tricycloalkenyl, phenyl, naphthyl, —$(C_{14})$aryl radical, each possibly being substituted by one or more radicals $R_z$;

each $R_1$, $R_2$, $R_3$, independently denotes $R_q$ or a —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$tricycloalkenyl, phenyl, naphthyl, —$(C_{14})$aryl radical, each possibly being substituted by one or more radicals $R_z$;

Rf is H, $(C_1$-$C_{12})$ alkyl optionally substituted by 1 to 5 radicals $R_y$, $(C_1$-$C_{12})$alkyl-O—$(C_1$-$C_{12})$alkyl, each $(C_1$-$C_{12})$ alkyl radical possibly being substituted by 1 to 5 groups $R_y$;

each $R_q$, independently is CN, OH, halogen, $N_3$, $NO_2$, $N(R_z)_2$, =$NR_z$, CH=$NR_z$, $NR_zOH$, $OR_z$, $COR_z$, $C(O)R_z$, $O(CO)OR_z$, $SR_z$, $S(O)R_z$ or $S(O)_2R_z$;

each $R_z$, independently is —$(C_1$-$C_6)$alkyl, —$(C_2$-$C_6)$alkenyl, —$(C_3$-$C_8)$cycloalkyl, —$(C_3$-$C_8)$cycloalkenyl, phenyl, a heterocycle having 3 to 5 branches, CH(halo)$_2$ or C(halo)$_3$; and n is equal to 0, 1, 2, 3, 4 or 5, and also the salts thereof, the optical isomers thereof, and/or the diastereoisomers thereof.

Some compounds of formula (I) may have assymetric centres and exist in different enantiomeric and diastereoisomeric forms. A compound of formula (I) may be in the form of an optical isomer or a diastereoisomer. According to the invention, the compounds of formula (I) also comprise their optical isomer or diastereoisomeric forms and mixtures thereof, including racemic mixtures.

"—$(C_1$-$C_{10})$alkyl" means a saturated, linear or branched non-cyclic hydrocarbon-based chain having from 1 to 10 carbon atoms. As examples of saturated linear —$(C_1$-$C_{10})$ alkyl radicals, mention may be made of: methyl, ethyl, n-propyl, n-butyl, n-pentyl, n-hexyl, n-heptyl, n-octyl, n-nonyl and n-decyl. As examples of saturated branched —$(C_1$-$C_{10})$alkyl radicals, mention may be made of isopropyl, sec-butyl, isobutyl, tert-butyl, isopentyl, 2-methylbutyl, 3-methylbutyl, 2,2-dimethylbutyl, 2,3-dimethylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, -3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, -2-methyl-4-ethylhexyl, 2,2-diethylpentyl, 3,3-diethylhexyl, 2,2-diethylhexyl, 3,3-diethylhexyl.

"—$(C_2$-$C_{10})$alkenyl" means an unsaturated, linear or branched non-cyclic hydrocarbon-based chain having from 2 to 10 carbon atoms and comprising at least one carbon-carbon double bond. As examples of —$(C_1$-$C_{10})$alkenyl radicals, mention may be made of: 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl.

"—$(C_2$-$C_{10})$alkynyl" means an unsaturated, linear or branched non-cyclic hydrocarbon-based chain having from 2 to 10 carbon atoms and comprising at least one carbon-carbon triple bond. As examples of —$(C_1$-$C_{10})$alkynyl radicals, mention may be made of: acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl.

"—$(C_3$-$C_{10})$cycloalkyl" means a saturated hydrocarbon-based ring having from 3 to 10 carbon atoms. As examples of —$(C_3$-$C_{10})$cycloalkyl radicals, mention may be made of: cyclopropyl, cyclobutyl, cyclopentyl, cyclohexyl, cycloheptyl, cyclooctyl, cyclononyl and cyclodecyl.

"—$(C_8$-$C_{14})$bicycloalkyl" means a hydrocarbon-based bicycle having from 8 to 14 carbon atoms and at least one saturated cycloalkyl ring. As examples of —$(C_8$-$C_{14})$bicycloalkyl radicals, mention may be made of indanyle, 1,2,3,4-tetrahydronaphthyl, 5,6,7,8-tetrahydronaphthyl and perhydronaphthyl.

"—$(C_8$-$C_{14})$tricycloalkyl" means a hydrocarbon-based tricycle having from 8 to 14 carbon atoms and at least one saturated cycloalkyl ring. As examples of —$(C_8$-$C_{14})$tricycloalkyl radicals, mention may be made of: pyrenyl, 1,2,3,4-tetrahydroanthracenyl, perhydroanthracenyl, aceanthrenyl, 1,2,3,4-tetrahydropenanthrenyl, 5,6,7,8-tetrahydrophenanthrenyl and perhydrophenanthrenyl.

"—$(C_5$-$C_{10})$cycloalkenyl" means a non-aromatic hydrocarbon-based cyclic radical having at least one carbon-carbon double bond in the ring system and from 5 to 10 carbon atoms. As examples of —$(C_5$-$C_{10})$cycloalkenyl radicals, mention may be made of: cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl.

"—($C_8$-$C_{14}$)bicycloalkenyl" means a hydrocarbon-based bicycle having at least one carbon-carbon double bond in each ring and from 8 to 14 carbon atoms. As examples of —($C_8$-$C_{14}$)bicycloalkenyl radicals, mention may be made of: indenyl, pentalenyl, naphthalenyl, azulenyl, heptalenyl, 1,2,7,8-tetrahydronaphthalenyl.

"—($C_8$-$C_{14}$)tricycloalkenyl" means a hydrocarbon-based tricycle having at least one carbon-carbon double bond in each ring and from 8 to 14 carbon atoms. As examples of —($C_8$-$C_{14}$)tricycloalkenyl radicals, mention may be made of: anthracenyl, phenalenyl, acenaphthalenyl, as-indacenyl, s-indacenyl.

"—($C_{14}$)aryl" means an aromatic carbocycle having 14 branches, such as anthryl and phenanthryl.

"Heterocycle having 3 to 5 branches" means a saturated, unsaturated, aromatic or non-aromatic heteromonocycle having 3 to 5 branches having carbon atoms and heteroatoms. A heterocycle having 3 or 4 branches may comprise up to 3 heteroatoms and a heterocycle having 5 branches may comprise up to 4 heteroatoms. Each heteroatom is independently chosen from a nitrogen, possibly quaternized, oxygen, and sulfur, including sulfoxide and sulfone. The heterocycle may be attached via any heteroatom or carbon atom. As examples of heterocycles having 3-5 branches, mention may be made of: furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl and tetrahydrothiophenyl.

"Halo" means a halogen atom such as F (fluorine), Cl (chlorine), Br (bromine) and I (iodine).

"—CH(halo)$_2$" means a methyl group in which 2 of the hydrogens are replaced by a halogen atom. Mention may be made, for example, of: —CHF$_2$, —CHCl$_2$, —CHBr$_2$, —CHBrCl, —CHClI and —CHI$_2$.

"—CH(halo)$_3$" means a methyl group in which 3 of the hydrogens are replaced by a halogen atom. Mention may be made, for example, of: —CF$_3$, —CF$_2$Cl, —CCl$_3$, —CBr$_3$, —CFBr$_2$ and —Cl$_3$.

"Salts of the compounds of formula (I)" means a salt formed by an inorganic or organic acid or else an inorganic or organic base.

As examples of acid salts, mention may be made of the sulfate, citrate, acetate, oxalate, chlorure, bromure, iodure, nitrate, bisulfate, phosphate, isonicotinate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As examples of base salts, mention may be made of hydroxides of alkali metals such as sodium, potassium and lithium; hydroxides of alkaline earth metals such as calcium and magnesium; hydroxides of other metals such as aluminium and zinc, aqueous ammonia and organic amines such as unsubstituted or hydroxy-substituted mono-, di- or tryalkylamines; dicyclohexylamines; tributylamines, pyridine, N-methyl-N-ethylamine; diethylamine; triethylamine; mono-, bis- or tris-(2-hydroxyalkylamines) such as mono-, bis- or tris-(2-hydroxyethyl)amine, 2-hydroxy-tert-butylamine or tris-(hydroxymethyl)methylamine, N,N-di-alkyl-N-(hydroxyalkyl)-amines, such as N,N-dimethyl-N-(2-hydroxyethyl)amine or tri-(2-hydroxyethyl)amine; N-methyl-D-glucamine; and amino acids such as arginine and lysine.

According to a preferred form of the invention, at least one of the radicals $X_1$, $X_2$, $X_3$, $X_4$, $X_5$, $X_a$, $X_b$, $X_c$, $X_d$, $X_e$ and $X_f$ is O.

According to a preferred form of the invention, at least one of the radicals $Y_1$, $Y_2$, $Y_3$, $Y_4$, $Y_5$, $Y_6$, independently denotes H.

According to a preferred form of the invention, at least one of the radicals $Y_1$, $Y_2$, $Y_3$, $Y_4$, $Y_6$, independently denotes $CH_3$.

According to a preferred form of the invention, $R_1$ denotes H or $CH_3$.

According to a preferred form of the invention, n is equal to 5.

According to a particularly preferred form, the composition of the invention comprises the baicalin corresponding to the following general formula (II):

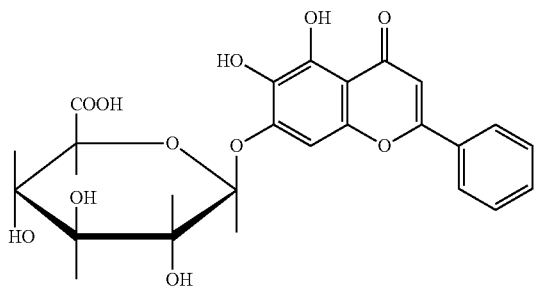

(II)

or a plant extract containing same.

This compound is described, especially, in application WO2008/140440, especially in the form of a solution. The baicalin may be used in the form of a solution comprising an alkyl glycol having 2 to 7 carbon atoms, a polyol ether, and at least one antioxidant. Such an organic compound may be obtained as described in EP1400579 (US2004/0067894), relating to the synthesis of tetrahydroxyflavones, the general formula of which comprises baicalin.

The baicalin may be used in the form of an extract of plant origin. Baicalin is a polyphenol (flavone) extracted especially from the scullcap root, in particular of *Scutellaria baicalensis*, with the INCI name: *SCUTELLARIA BAICALENSIS* ROOT EXTRACT. It originates in traditional Chinese medicine. The various methods for preparing the extracts are described in the application WO2005044281.

The baicalin is especially available from MMP under the trade name BAICALIN 95 MM® by MMP.

The baicalin of formula (II) and/or one of the compounds of formula (I) are preferably present in the compositions according to the invention in active material concentrations ranging from 0.01 to 10% by weight, better still from 0.1% to 5% by weight, even more preferably from 0.2 to 5% by weight relative to the total weight of the composition.

Vitamin B3 and the Derivatives Thereof

"Vitamin B3" means any molecule having the general formula:

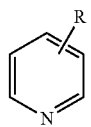

in which R is —CONH$_2$ (i.e., niacinamide, isoniacinamide), —COOH (i.e.: nicotinic acid), or —CH$_2$OH (i.e.: nicotinyl alcohol) and also the derivatives thereof and the organic or inorganic acid salts thereof or the inorganic or organic base salts thereof, such as those mentioned above.

As examples of vitamin B3 derivatives, mention may be made of:

- esters of nicotinic acid, such as those with the following INCI names: Niacinamide Ascorbate, Niacinamide Glycolate, Niacinamide Hydroxybenzoate, Niacinamide Hydroxycitrate, Niacinamide Lactate, Niacinamide Malate, Niacinamide Mandalate, Niacinamide Salicylate, Niacinamide Thioctate, supplied by Bioderma Tech. Co LTD;
- quaternary ammonium salts such as Methyl Niacinamide Chloride (INCI name) such as the commercial product MNA Chloride® from Pharmena;
- the reaction products of niacinamide with polypeptides such as those derived from yeasts: INCI name Niacinamide/Yeast Polypeptide such as the commercial product sold under the trade name Vitazyme B3® by Arch Personal Care Products, L.P./Lonza Personal Care.

Use will more particularly be made of niacinamide, such as the commercial products sold under the name Niacinamide PC® (DSM Nutritional Products, Inc.)

OriStar NA® (Orient Stars LLC)

RonaCare Nicotinamide® (Merck KGaA/EMD Chemicals)

RonaCare Nicotinamide® (EMD Chemicals)

The vitamin B3 and/or a derivative thereof are preferably present in the compositions according to the invention in active material concentrations ranging from 0.01 to 20% by weight, better still from 0.1 to 10% by weight, even more preferably from 0.5 to 5% by weight relative to the total weight of the composition.

Xanthine Base

The compositions according to the invention comprise at least one xanthine base and/or a plant extract containing same.

Among the xanthine bases of use according to the invention, mention may be made of: caffeine, theophylline, theobromine, acefylline, xanthinol nicotinate, diniprophylline, diprophylline, etamiphylline and derivatives thereof, etophylline, proxyphylline, pentophylline, propentophylline, pyridophylline and bamiphylline, without this list being limiting.

Preference is given, in particular, to using caffeine, theophylline, theobromine and acefylline, and more particularly caffeine.

As examples of plant extracts containing xanthine bases, mention may especially be made of extracts of tea, coffee, guarana, mate and cola, without this list being limiting.

The xanthine base may be present in the composition according to the invention in a content of active material ranging from 0.01% to 10% by weight, relative to the total weight of the composition, preferably ranging from 0.1 to 7% by weight, and preferentially ranging from 0.1 to 3% by weight, more particularly ranging from 1 to 3% by weight.

Polyvalent Cation Salt

The polyvalent cations in accordance with the invention are inorganic and are preferably chosen from:

- alkaline earth metals, such as beryllium, magnesium, calcium, strontium or barium;
- transition metal cations, such as titanium (Ti$^{2+}$, Ti$^{3+}$, Ti$^{4+}$), manganese (Mn$^{2+}$, Mn$^{3+}$, Mn$^{4+}$, Mn$^{7+}$), zinc (Zn$^{2+}$), zirconium (Zr$^{4+}$), hafnium (Hf$^{4+}$), or aluminium (Al$^{3+}$).

The preferential alkaline earth cations will be chosen from magnesium and calcium.

The preferential transition metal cations will be chosen from zinc, manganese and aluminium.

Among the cation salts of use according to the invention, mention may be made of halides.

The halogens are a chemical series constituted of the chemical elements from Group 17 of the Periodic Table, also known as Group VII or VIIA. Use will be made, as halides, of fluorides (fluorine), chlorides (chlorine), bromides (bromine) and iodides (iodine) and more particularly chlorides.

Mention may be made of carboxylic acid salts, such as acetates, propionates, pyrrolidone carboxylates (or pidolates) or sorbates; polyhydroxylated carboxylic acid salts, such as gluconates, heptagluconates, ketogluconates, lactate gluconates, ascorbates or pantothenates; monocarboxylic or polycarboxylic hydroxy acid salts, such as citrates or lactates; amino acid salts, such as aspartates or glutamates; or fulvate salts.

Mention may also be made of bicarbonates, also known as hydrogen carbonates.

Mention may also be made of sulfate (SO4) salts, such as magnesium sulfate, double sulfate salts, such as aluminium double sulfates, such as alum: KAl(SO4)$_2$.

Mention may also be made of nitrates, such as calcium nitrates; Ca(NO$_3$)$_2$.

Use will more particularly be made of the chlorides and sulfates of alkaline earth metals and more particularly those of magnesium and of calcium, and even more particularly magnesium sulfate, calcium chloride, and mixtures thereof.

The polyvalent metal cation salt(s) are preferably present in the composition according to the invention in a content ranging from 0.01% to 2% by weight, relative to the total weight of the composition, preferably ranging from 0.1% to 1.5% by weight and preferentially ranging from 0.5% to 1% by weight.

Aqueous Phase

The aqueous phase comprises water and optionally water-soluble or water-miscible ingredients, such as water-soluble solvents.

A water that is suitable for use in the invention may be a floral water such as cornflower water and/or a mineral water such as Vittel water, Lucas water or La Roche Posay water and/or a spring water.

In the present invention, the term "water-soluble solvent" denotes a compound that is liquid at room temperature and water-miscible (miscibility with water of greater than 50% by weight at 25° C. and atmospheric pressure).

The water-soluble solvents of use in the composition of the invention may also be volatile.

Among the water-soluble solvents that may be used in the composition in accordance with the invention, mention may be made especially of lower monoalcohols having from 1 to 5 carbon atoms such as ethanol and isopropanol, glycols having from 2 to 8 carbon atoms such as ethylene glycol, propylene glycol, 1,3-butylene glycol and dipropylene glycol, C$_3$ and C$_4$ ketones and C$_2$-C$_4$ aldehydes.

The aqueous phase is preferably present in a concentration of at least 20.0% by weight, preferably ranging from 30 to 60% by weight, more particularly from 40 to 50% by weight relative to the total weight of said composition.

Oily Phase

The composition of the invention comprises a continuous oily phase. Said phase is liquid (in the absence of structuring agent) at room temperature (20-25° C.). It is organic and water-immiscible.

The oily phase (or fatty phase) of the compositions according to the invention comprises at least one oil. It may be constituted of a single oil or of a mixture of several oils.

The term "oil" means any fatty substance in the liquid form at room temperature (20-25° C.) and at atmospheric pressure. These oils may be of plant, mineral or synthetic origin.

According to one embodiment, the oils are chosen from the group constituted of hydrocarbon-based oils, silicone oils, fluoro oils and mixtures thereof.

The term "oil" means a fatty substance which is liquid at room temperature (25° C.) and atmospheric pressure (760 mmHg, i.e. $10^5$ Pa). The oil may be volatile or non-volatile.

Within the meaning of the present invention, "silicone oil" means an oil comprising at least one silicon atom and especially at least one Si—O group, and more particularly an organopolysiloxane.

The term "fluoro oil" means an oil comprising at least one fluorine atom.

The term "hydrocarbon-based oil" means an oil mainly containing hydrogen and carbon atoms and optionally one or more functions chosen from hydroxyl, ester, ether and carboxylic functions.

For the purposes of the invention, the term "volatile oil" means any oil that is capable of evaporating on contact with the skin in less than one hour, at room temperature and atmospheric pressure. The volatile oil is a volatile cosmetic compound which is liquid at room temperature, especially having a nonzero vapour pressure, at room temperature and atmospheric pressure, especially having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The total concentration of oily phase of the composition of the invention preferably ranges from 40 to 95% by weight, more particularly ranging from 50 to 70% by weight, relative to the total weight of the composition.

Volatile Oils

According to one embodiment, the oily phase of the compositions of the invention comprises at least one volatile oil. The oily phase of the compositions of the invention may comprise a mixture of several volatile oils.

The volatile oils may be hydrocarbon-based, silicone or fluoro oils.

The volatile oils may be chosen from hydrocarbon-based oils having from 8 to 16 carbon atoms, and especially branched $C_8$-$C_{16}$ alkanes (also referred to as isoparaffins or isoalkanes), such as isododecane (also referred to as 2,2,4,4,6-pentamethylheptane), isodecane, isohexadecane and, for example, the oils sold under the trade names Isopar® or Permethyl®.

As volatile hydrocarbon-based oil, mention may also be made of linear $C_9$-$C_{17}$ alkanes, such as dodecane ($C_{12}$) and tetradecane ($C_{14}$), sold respectively under the references PARAFOL® 12-97 and PARAFOL® 14-97 (Sasol) and such as the alkanes obtained according to the process described in international application WO 2007/068371 A1, such as the mixture of undecane ($C_{11}$) and tridecane ($C_{13}$).

According to one embodiment, the oily phase of the compositions of the invention comprises at least one volatile silicone oil.

As volatile silicone oils, use may also be made of volatile silicones such as, for example, volatile linear or cyclic silicone oils, especially those having a viscosity of less than or equal to 8 centistokes (cSt) ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oil of use in the invention, mention may especially be made of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

More particularly, as volatile silicone oil, mention may be made of linear or cyclic silicone oils having from 2 to 7 silicon atoms, these silicones optionally comprising alkyl or alkoxy groups having from 1 to 10 carbon atoms.

As volatile fluoro oil, mention may be made, for example, of nonafluoromethoxybutane or perfluoromethylcyclopentane, and mixtures thereof.

According to a particular form of the invention, the oily phase comprises at least one non-cyclic volatile silicone oil.

Non-Cyclic Volatile Silicone Oils

The non-cyclic volatile silicone oils according to the invention are preferably chosen from:

the non-cyclic linear silicones of formula (II):

$$R_3SiO-(R_2SiO)_n-SiR_3 \quad (II)$$

in which R, which may be identical or different, denotes:
a saturated or unsaturated hydrocarbon-based radical, containing from 1 to 10 carbon atoms and preferably from 1 to 6 carbon atoms, optionally substituted with one or more fluorine atoms or with one or more hydroxyl groups, or
a hydroxyl group,
one of the radicals R possibly being a phenyl group,
n is an integer ranging from 0 to 8, preferably ranging from 2 to 6 and better still ranging from 3 to 5, the silicone compound of formula (II) containing at most 15 carbon atoms.

the branched silicones of formula (III) or (IV) below:

$$R_3SiO-[(R_3SiO)RSiO]-(R_2SiO)x-SiR_3 \quad (III)$$

$$[R_3SiO]_4Si \quad (IV)$$

in which R, which may be identical or different, denotes:
a saturated or unsaturated hydrocarbon-based radical having from 1 to 10 carbon atoms, optionally substituted with one or more fluorine atoms or with one or more hydroxyl groups, or
a hydroxyl group,
one of the radicals R possibly being a phenyl group,
x is an integer ranging from 0 to 8,
the silicone compound of formula (III) or (IV) containing at most 15 carbon atoms.

Preferably, for the compounds of formulae (II), (III) and (IV), the ratio between the number of carbon atoms and the number of silicon atoms is between 2.25 and 4.33.

The silicones of formulae (II) to (IV) may be prepared according to the known processes for synthesizing silicone compounds.

Examples of non-cyclic volatile silicone of use according to the invention are indicated below; these silicones may be used alone or in a mixture.

Among the silicones of formula (II), mention may be made of:

a) the following disiloxanes (L2):
hexamethyldisiloxane, especially sold under the name DC 200 FLUID 0.65 cst by Dow Corning
1,3-di-tert-butyl-1,1,3,3-tetramethyldisiloxane;
1,3-dipropyl-1,1,3,3-tetramethyldisiloxane;
heptylpentamethyldisiloxane;
1,1,1-triethyl-3,3,3-trimethyldisiloxane;
hexaethyldisiloxane;
1,1,3,3-tetramethyl-1,3-bis(2-methylpropyl)disiloxane;
pentamethyloctyldisiloxane;
1,1,1-trimethyl-3,3,3-tris(1-methylethyl)disiloxane;
1-butyl-3-ethyl-1,1,3-trimethyl 3-propyldisiloxane;
pentamethylpentyldisiloxane;
1-butyl-1,1,3,3-tetramethyl-3-(1-methylethyl)disiloxane;
1,1,3,3-tetramethyl-1,3-bis(1-methylpropyl)disiloxane;
1,1,3-triethyl-1,3,3-tripropyldisiloxane;
(3,3-dimethylbutyl)pentamethyldisiloxane;
(3-methylbutyl)pentamethyldisiloxane;
(3-methylpentyl)pentamethyldisiloxane;
1,1,1-triethyl-3,3,3-dimethyl-3-propyldisiloxane;
1-(1,1-dimethylethyl)-1,1,3,3,3-pentamethyldisiloxane;
1,1,1-trimethyl-3,3,3-tripropyldisiloxane;
1,3-dimethyl-1,1,3,3-tetrakis(1-methylethyl)disiloxane;
1,1-dibutyl-1,3,3,3-tetramethyldisiloxane;
1,1,3,3-tetramethyl-1,3-bis(1-methylethyl)disiloxane;
1,1,1,3-tetramethyl-3,3-bis(1-methylethyl)disiloxane;
1,1,1,3-tetramethyl-3,3-dipropyldisiloxane;
1,1,3,3-tetramethyl-1,3-bis(3-methylbutyl)disiloxane;
butylpentamethyldisiloxane;
pentaethylmethyldisiloxane;
1,1,3,3-tetramethyl-1,3-dipentyldisiloxane;
1,3-dimethyl-1,1,3,3-tetrapropyldisiloxane;
1,1,1,3-tetraethyl-3,3-dimethyldisiloxane;
1,1,1-triethyl-3,3,3-tripropyldisiloxane;
1,3-dibutyl-1,1,3,3-tetramethyldisiloxane;
hexylpentamethyldisiloxane;

b) the following trisiloxanes (L3):
octamethyltrisiloxane, especially sold under the name Xiameter PMX-200 Silicone Fluid 1 CS by Dow Corning;
3-pentyl-1,1,1,3,5,5,5-heptamethyltrisiloxane;
1-hexyl-1,1,3,3,5,5,5-heptamethyltrisiloxane;
1,1,1,3,3,5,5-heptamethyl-5-octyltrisiloxane;
1,1,1,3,5,5,5-heptamethyl-3-octyltrisiloxane, especially sold under the name Silsoft 034 by OSI;
1,1,1,3,5,5,5-heptamethyl-3-hexyltrisiloxane, especially sold under the name DC 2-1731 by Dow Corning;
1,1,3,3,5,5-hexamethyl-1,5-dipropyltrisiloxane;
3-(1-ethylbutyl)-1,1,1,3,5,5,5-heptamethyltrisiloxane;
1,1,1,3,5,5,5-heptamethyl-3-(1-methylpentyl)trisiloxane;
1,5-diethyl-1,1,3,3,5,5-hexamethyltrisiloxane;
1,1,1,3,5,5,5-heptamethyl-3-(1-methylpropyl)trisiloxane;
3-(1,1-dimethylethyl)-1,1,1,3,5,5,5-heptamethyltrisiloxane;
1,1,1,5,5,5-hexamethyl-3,3-bis(1-methylethyl)trisiloxane;
1,1,1,3,3,5,5-heptamethyl-1,5-bis(1-methylpropyl)trisiloxane;
1,5-bis(1,1-dimethylethyl)-1,1,3,3,5,5-hexamethyltrisiloxane;
3-(3,3-dimethylbutyl-1,1,1,3,5,5,5-heptamethyltrisiloxane;
1,1,1,3,5,5,5-heptamethyl-3-(3-methylbutyl)trisiloxane;
1,1,1,3,5,5,5-heptamethyl-3-(3-methylpentyl)trisiloxane;
1,1,1,3,5,5,5-heptamethyl-3-(2-methylpropyl)trisiloxane;
1-butyl-1,1,3,3,5,5,5-heptamethyltrisiloxane;
1,1,1,3,5,5,5-heptamethyl-3-propyltrisiloxane;
3-isohexyl-1,1,1,3,5,5,5-heptamethyltrisiloxane;
1,3,5-triethyl 1,1,3,5,5-pentamethyltrisiloxane;
3-butyl-1,1,1,3,5,5,5-heptamethyltrisiloxane;
3-tert-pentyl-1,1,1,3,5,5,5-heptamethyltrisiloxane;
1,1,1,5,5,5-hexamethyl-3,3-dipropyltrisiloxane;
3,3-diethyl-1,1,1,5,5,5-hexamethyltrisiloxane;
1,5-dibutyl-1,1,3,3,5,5-hexamethyltrisiloxane;
1,1,1,5,5,5-hexaethyl-3,3-dimethyltrisiloxane;
3,3-dibutyl-1,1,1,5,5,5-hexamethyltrisiloxane;
3-ethyl-1,1,1,3,5,5,5-heptamethyltrisiloxane;
3-heptyl-1,1,1,3,5,5,5-heptamethyltrisiloxane;
1-ethyl-1,3,3,5,5,5-heptamethyltrisiloxane;

c) the following tetrasiloxanes (L4):
decamethyltetrasiloxane;
1,1,3,3,5,5,7,7-octamethyl-1,7-dipropyltetrasiloxane;
1,1,1,3,3,5,7,7,7-nonamethyl-5-(1-methylethyl)tetrasiloxane;
1-butyl-1,1,3,3,5,5,7,7,7-nonamethyltetrasiloxane;
3,5-diethyl-1,1,1,3,5,7,7,7-octamethyltetrasiloxane;
1,3,5,7-tetraethyl-1,1,3,5,7,7-hexamethyltetrasiloxane;
3,3,5,5-tetraethyl-1,1,1,7,7,7-hexamethyltetrasiloxane;
1,1,1,3,3,5,5,7,7-nonamethyl-7-phenyltetrasiloxane;
3,3-diethyl-1,1,1,5,5,7,7,7-octamethyltetrasiloxane;
1,1,1,3,3,5,7,7,7-nonamethyl-5-phenyltetrasiloxane;

d) the following pentasiloxanes (L5):
dodecamethylpentasiloxane;
1,1,3,3,5,5,7,7,9,9-decamethyl-1,9-dipropylpentasiloxane;
3,3,5,5,7,7-hexaethyl-1,1,1,9,9,9-hexamethylpentasiloxane;
1,1,1,3,3,5,7,7,9,9-undecamethyl-5-phenylpentasiloxane;
1-butyl-1,1,3,3,5,5,7,7,9,9,9-undecamethylpentasiloxane;
3,3-diethyl 1,1,1,5,5,7,7,9,9,9-decamethylpentasiloxane;
1,3,5,7,9-pentaethyl-1,1,3,5,7,9,9-heptamethylpentasiloxane;
3,5,7-triethyl-1,1,1,3,5,7,9,9,9-nonamethylpentasiloxane;
1,1,1-triethyl-3,3,5,5,7,7,9,9,9-nonamethylpentasiloxane;

e) the following hexasiloxanes (L6):
1-butyl-1,1,3,3,5,5,7,7,9,9,11,11,11-tridecamethylhexasiloxane;
3,5,7,9-tetraethyl-1,1,1,3,5,7,9,11,11,11-decamethylhexasiloxane;
tetradecamethylhexasiloxane;

f) hexadecamethylheptasiloxane (L7);

g) octadecamethyloctasiloxane (L8).

Among the silicones of formula (III), mention may be made of:

a) the following tetrasiloxanes (L4):
2-[3,3,3-trimethyl-1,1-bis[(trimethylsylil)oxy]disiloxanyl]ethyl;
1,1,1,5,5,5-hexamethyl 3-(2-methylpropyl) 3-[(trimethylsilyl)oxy]trisiloxane;
3-(1,1-dimethylethyl)-1,1,1,5,5,5-hexamethyl 3-[(trimethylsilyl)oxy]trisiloxane;
3-butyl-1,1,1,5,5,5-hexamethyl-3-[(trimethylsilyl)oxy]trisiloxane;
1,1,1,5,5,5-hexamethyl-3-propyl-3-[(trimethylsilyl)oxy]trisiloxane;
3-ethyl-1,1,1,5,5,5-hexamethyl-3-[(trimethylsilyl)oxy]trisiloxane;
1,1,1-triethyl 3,5,5,5-tetramethyl-3-(trimethylsiloxy)trisiloxane;
3-methyl-1,1,1,5,5,5-hexamethyl-3-[(trimethylsilyl)oxy]trisiloxane;
3-[(dimethylphenylsilyl)oxy]-1,1,1,3,5,5,5-heptamethyl-
1,1,1,5,5,5-hexamethyl-3-(2-methylpentyl)-3-[(trimethylsilyl)oxy]trisiloxane;

1,1,1,5,5,5-hexamethyl-3-(4-methylpentyl)-3-[(trimethylsilyl)oxy]trisiloxane;
3-hexyl-1,1,1,5,5,5-hexamethyl-3-[(trimethylsilyl)oxy]trisiloxane;
1,1,1,3,5,5,5-heptamethyl-3-[(trimethylsilyl)oxy]trisiloxane;
  b) the following pentasiloxanes (L5):
1,1,1,3,5,5,7,7,7-nonamethyl-3-(trimethylsiloxy)tetrasiloxane;
1,1,1,3,3,7,7,7-octamethyl-5-phenyl-5-[(trimethylsilyl)oxy]tetrasiloxane;
  c) the following heptasiloxanes (L7):
1,1,1,3,5,5,7,7,9,9,11,11,11-tridecamethyl-3-[(trimethylsilyl)oxy]hexasiloxane.

Among the silicones of formula (IV), mention may be made of:
1,1,1,5,5,5-hexamethyl-3,3-bis(trimethylsiloxy)trisiloxane.

Use may also be made of other volatile silicone oils chosen from:
  a) the following tetrasiloxanes (L4):
2,2,8,8-tetramethyl-5-[(pentamethyldisiloxanyl)methyl]-3,7-dioxa-2,8-disilanonane;
2,2,5,8,8-pentamethyl-5-[(trimethylsilyl)methoxy]-4,6-dioxa-2,5,8-trisilanonane;
1,3-dimethyl-1,3-bis[(trimethylsilyl)methyl]-1,3-disiloxanediol;
3-ethyl-1,1,1,5,5,5-hexamethyl-3-[3-(trimethylsiloxy)propyl]trisiloxane;
1,1,1,5,5,5-hexamethyl-3-phenyl-3-[(trimethylsilyl)oxy]trisiloxane (Dow 556 Fluid);
  b) the following pentasiloxanes (L5):
2,2,7,7,9,9,11,11,16,16-decamethyl-3,8,10,15-tetraoxa-2,7,9,11,16-pentasilaheptadecane;
tetrakis[(trimethylsilyl)methyl]silicic acid ester;
  c) the following hexasiloxanes (L6):
3,5-diethyl 1,1,1,7,7,7-hexamethyl-3,5-bis[(trimethylsilyl)oxy]tetrasiloxane;
1,1,1,3,5,7,7,7-octamethyl-3,5-bis[(trimethylsilyl)oxy]tetrasiloxane;
  d) heptasiloxane (L7):
1,1,1,3,7,7,7-heptamethyl-3,5,5-tris[(trimethylsilyl)oxy]tetrasiloxane;
  e) the following octasiloxanes (L8):
1,1,1,3,5,5,9,9,9-nonamethyl-3,7,7-tris[(trimethylsilyl)oxy]pentasiloxane;
1,1,1,3,5,7,9,9,9-nonamethyl-3,5,7-tris[(trimethylsilyl)oxy]pentasiloxane;
1,1,1,7,7,7-hexamethyl-3,3,5,5-tetrakis[(trimethylsilyl)oxy]tetrasiloxane.

The non-cyclic volatile silicone oils according to the invention preferably have a viscosity at 25° C. ranging from 0.5 to 8 centistokes (from 0.5 to 8 mm³/s). The viscosity measurement method used in the invention to characterize the silicone oils according to the invention may be the "kinematic viscosity at 25° C. raw product CID-012-01" or even the "Ubbelohde viscosity at 25° C. DIN 51562-1 PV04001".

Among the non-cyclic volatile silicone oils according to the invention, linear non-cyclic volatile silicone oils will more particularly be chosen, and more particularly:
  octamethyltrisiloxane, especially sold under the name Xiameter PMX-200 Silicone Fluid 1CS by Dow Corning;
  decamethyltetrasiloxane, especially sold under the name Xiameter PMX-200 Silicone Fluid 1.5CS® by Dow Corning;
  dodecamethylpentasiloxane, such as the commercial products sold under the names KF-96L-2CS®, DM-FLUID-2CS® by Shin Etsu; BERB-DM2® by BRB International or Silicone Fluid 2CS® by Dow Corning,
  mixtures thereof, and more particularly dodecamethylpentasiloxane.

Non-Volatile Oils

The non-volatile oils may especially be chosen from non-volatile hydrocarbon-based, fluoro and/or silicone oils.

As non-volatile hydrocarbon-based oil, mention may especially be made of: hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203); triglycerides constituted of fatty acid esters of glycerol, in particular the fatty acids of which may have chain lengths ranging from $C_4$ to $C_{36}$, and especially from $C_{18}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camelina oil, canola oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, squash oil, pumpkin oil, musk rose oil, sesame oil, soybean oil, sunflower oil, castor oil and watermelon oil, and mixtures thereof, or alternatively caprylic/capric acid triglycerides, such as those sold by Stéarineries Dubois or those sold under the names Miglyol 810®, 812® and 818® by Dynamit Nobel;

linear or branched hydrocarbons, of mineral or synthetic origin, such as liquid paraffins and derivatives thereof, petroleum jelly, polydecenes, polybutenes, hydrogenated polyisobutene such as Parleam, or squalane;

synthetic ethers containing from 10 to 40 carbon atoms, such as dicaprylyl ether;

synthetic esters, such as oils of formula $R^1COOR^2$, in which $R^1$ represents a residue of a linear or branched fatty acid comprising from 1 to 40 carbon atoms, and $R^2$ represents a hydrocarbon-based chain, especially branched, containing from 1 to 40 carbon atoms with the proviso that the sum of the number of carbon atoms of the chains $R^1$ and $R^2$ is greater than or equal to 10; the esters may be chosen especially from fatty acid esters of alcohols, such as cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, such as isostearyl lactate, octyl hydroxystearate, diisopropyl adipate, heptanoates, and especially isostearyl heptanoate, alcohol or polyalcohol octanoates, decanoates or ricinoleates, such as propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, such as isodecyl neopentanoate, isotridecyl neopentanoate, isostearyl neopentanoate, octyldodecyl neopentanoate, isononanoic acid esters, such as isononyl isononanoate, isotridecyl isononanoate, octyl isononanoate, hydroxylated esters, such as isostearyl lactate and diisostearyl malate;

polyol esters and pentaerythritol esters, such as dipentaerythrityl tetrahydroxystearate/tetraisostearate;

esters of diol dimers and of diacid dimers, such as Lusplan DD-DA5® and Lusplan DD-DA7® sold by Nippon Fine Chemical and described in application US 2004/175338;

copolymers of a diol dimer and of a diacid dimer and esters thereof, such as dilinoleyl diol dimer/dilinoleic dimer copolymers and esters thereof, for instance Plandool-G;

copolymers of polyols and of diacid dimers, and esters thereof, such as Hailuscent ISDA or the dilinoleic acid/butanediol copolymer;

fatty alcohols that are liquid at room temperature, with a branched and/or unsaturated carbon-based chain having from 12 to 26 carbon atoms, such as 2-octyldodecanol, isostearyl alcohol, oleyl alcohol, 2-hexyldecanol, 2-butyloctanol and 2-undecylpentadecanol;

higher $C_{12}$-$C_{22}$ fatty acids, such as oleic acid, linoleic acid or linolenic acid, and mixtures thereof;

dialkyl carbonates, the two alkyl chains possibly being identical or different, such as the dicaprylyl carbonate sold under the name Cetiol CC® by Cognis;

oils of high molar mass, in particular having a molar mass ranging from approximately 400 to approximately 10 000 g/mol, in particular from approximately 650 to approximately 10 000 g/mol, in particular from approximately 750 to approximately 7500 g/mol and more particularly ranging from approximately 1000 to approximately 5000 g/mol. As oil of high molar mass of use in the present invention, mention may be made especially of oils chosen from:

lipophilic polymers, linear fatty acid esters having a total carbon number ranging from 35 to 70, hydroxylated esters, aromatic esters, $C_{24}$-$C_{28}$ branched fatty acid or fatty alcohol esters, silicone oils, oils of plant origin, and mixtures thereof;

fluorinated oils which are optionally partially hydrocarbon-based and/or silicone-based, such as fluorosilicone oils, fluorinated polyethers or fluorinated silicones, such as described in the document EP-A-847 752;

silicone oils, such as linear or cyclic non-volatile polydimethylsiloxanes (PDMSs);

polydimethylsiloxanes comprising alkyl, alkoxy or phenyl groups, which are pendant or at the end of a silicone chain, groups having from 2 to 24 carbon atoms, such as caprylyl methicone; phenyl silicones, such as phenyl trimethicones, phenyl dimethicones, phenyltrimethylsiloxydiphenylsiloxanes, diphenyl dimethicones, diphenylmethyldiphenyltrisiloxanes and 2-phenylethyltrimethylsiloxysilicates; and mixtures thereof.

Among the linear or branched hydrocarbons of mineral or synthetic origin, use is preferably made of paraffin oils or liquid petroleum jelly.

Among the hydrocarbon oils of plant origin, mention may preferably be made of plant oils, such as sweet almond oil, jojoba oil or macadamia oil.

According to one particular form, the hydrocarbon-based oils may be constituted of liquid organic UVB-screening agents.

The liposoluble liquid organic UVB-screening agents of use according to the invention are preferably chosen from liquid lipophilic β,β-diphenylacrylate compounds liquid lipophilic salicylate compounds liquid lipophilic cinnamate compounds and mixtures thereof.

β,β-Diphenylacrylate Compounds

Among these compounds, the following compounds are more particularly preferred:

2-ethylhexyl α-cyano-β,β-diphenylacrylate, ethyl α-cyano-β,β-diphenylacrylate such as Etocrylene, sold in particular under the trade name Uvinul N35® by BASF, 2-ethylhexyl β,β-diphenylacrylate, ethyl β,β-di(4'-methoxyphenyl)acrylate.

Among these compounds, preference is given even more particularly to the compound 2-ethylhexyl 2-cyano-3,3-diphenylacrylate, sold especially under the trade name Uvinul N539 by BASF.

Salicylate Compounds

Among the liquid lipophilic salicylate compounds of use according to the invention, mention may be made of:

Homosalate sold under the name Eusolex HMS by Rona/EM Industries,

Ethylhexyl salicylate, sold under the name Neo Heliopan OS by Symrise.

Cinnamate Compounds

Among the liquid lipophilic cinnamate compounds of use according to the invention, mention may be made of:

Ethylhexyl Methoxycinnamate, sold especially under the trade name Parsol MCX by DSM Nutritional Products, Isopropyl Methoxycinnamate, Isoamyl Methoxycinnamate, sold under the trade name Neo Heliopan E 1000 by Symrise.

Among the liquid liposoluble UVB-screening agents according to the invention, use will preferably be made of the compounds chosen from:

octocrylene, homosalate, ethylhexyl salicylate, ethylhexyl methoxycinnamate, and mixtures thereof.

Among these liquid liposoluble UVB-screening agents, use will more preferentially be made of the compounds chosen from:

octocrylene, ethylhexyl salicylate, homosalate, and mixtures thereof.

According to one preferential form of the invention, said mixture of β,β-diphenylacrylate/salicylate screening agents will be present in the composition of the invention at a concentration of at least 15% by weight, and more preferentially at a concentration of at least 20% by weight relative to the total weight of the composition.

Preferably, said mixture of β,β-diphenylacrylate/salicylate screening agents is used in concentrations ranging from 15 to 40% by weight, and more preferentially ranging from 20 to 30% by weight relative to the total weight of the composition.

Emulsifiers

The water-in-oil emulsions according to the invention generally comprise one or more emulsifying surfactants, which are preferably non-ionic.

For the purposes of the present invention, "emulsifying surfactant" means an amphiphilic surfactant compound, i.e. one which has two parts of different polarity. Generally, one is lipophilic (soluble or dispersible in an oily phase). The other is hydrophilic (soluble or dispersible in water). The emulsifying surfactants are characterized by the value of their HLB (Hydrophilic-Lipophilic Balance), the HLB being the ratio between the hydrophilic part and the lipophilic part in the molecule. The term "HLB" is well known to those skilled in the art and is described, for example, in "The HLB system. A time-saving guide to Emulsifier Selection" (published by ICI Americas Inc., 1984). For the emulsifying surfactants, the HLB generally ranges from 3 to 8 for the preparation of W/O emulsions. The HLB of the surfactant(s) used according to the invention may be determined via the Griffin method or the Davies method.

As examples of W/O emulsifying surfactants, mention may be made of alkyl esters or ethers of sorbitan, of glycerol, of polyol or of sugars; silicone surfactants, such as dimethicone copolyols, such as that having the INCI name Dimethicone (and) PEG/PPG-18/18 Dimethicone sold under the brand X-22-6711D® by Shin Etsu, the mixture of cyclomethicone and of dimethicone copolyol, sold under the name DC 5225 C® by Dow Corning, and alkyldimethicone copolyols such as laurylmethicone copolyol sold under the name Dow Corning 5200 Formulation Aid by Dow Corning; cetyl dimethicone copolyol, such as cetyl PEG/PPG-10/1 dimethicone, such as the product sold under the name Abil EM 90® by Evonik Goldschmidt, and the mixture of cetyl dimethicone copolyol, of polyglyceryl isostearate (4 mol) and of hexyl laurate, sold under the name Abil WE O9® by Goldschmidt. One or more coemulsifiers, which may be chosen advantageously from the group comprising polyol alkyl esters, may also be added thereto.

Mention may also be made of non-silicone emulsifying surfactants, especially alkyl esters or ethers of sorbitan, of glycerol, of polyol or of sugars.

As polyol alkyl esters, mention may especially be made of polyethylene glycol esters, such as PEG-30 dipolyhydroxystearate, such as the product sold under the name Cithrol DPHS-SO-(MV) by Croda.

As glycerol and/or sorbitan esters, mention may be made, for example, of polyglyceryl isostearate (INCI name: Polyglyceryl-4 Isostearate), such as the product sold under the name Isolan GI 34® by Evonik Goldschmidt; sorbitan isostearate, such as the product sold under the name Arlacel 987® by ICI; sorbitan glyceryl isostearate, such as the product sold under the name Arlacel 986® by ICI, the diester of a mixture of isostearic, polyhydroxystearic and sebacic acids with Polyglycerin-4 (INCI name: Polyglyceryl-4 Diisostearate/Polyhydroxystearate/Sebacate), such as the product sold under the name Isolan GPS® by Evonik, and mixtures thereof.

According to one particular form of the invention, the emulsifying surfactant can be chosen from emulsifying silicone elastomers.

The term "silicone elastomer" is intended to mean a supple, deformable organopolysiloxane that has viscoelastic properties and especially the consistency of a sponge or a supple sphere. Its modulus of elasticity is such that this material withstands deformation and has a limited ability to extend and to contract. This material is capable of regaining its original shape after stretching.

The emulsifying silicone elastomer may be chosen from polyoxyalkylenated silicone elastomers and polyglycerolated silicone elastomers, and mixtures thereof.

a) Polyoxyalkylenated Silicone Elastomers

The polyoxyalkylenated silicone elastomer is a crosslinked organopolysiloxane that may be obtained by a crosslinking addition reaction of diorganopolysiloxane containing at least one hydrogen bonded to silicon and of a polyoxyalkylene having at least two ethylenically unsaturated groups.

Preferably, the polyoxyalkylenated crosslinked organopolysiloxane is obtained by a crosslinking addition reaction (A1) of diorganopolysiloxane containing at least two hydrogens each bonded to a silicon, and (B1) of polyoxyalkylene having at least two ethylenically unsaturated groups, especially in the presence (C1) of a platinum catalyst, as described, for example, in U.S. Pat. Nos. 5,236,986 and 5,412,004.

In particular, the organopolysiloxane may be obtained by reaction of dimethylvinylsiloxy-terminated polyoxyalkylene (especially polyoxyethylene and/or polyoxypropylene) and of trimethylsiloxy-terminated methylhydropolysiloxane, in the presence of a platinum catalyst.

The organic groups bonded to the silicon atoms of compound (A1) may be alkyl groups having from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from trimethylsiloxy-terminated methylhydropolysiloxanes, trimethylsiloxy-terminated dimethylsiloxane/methylhydrosiloxane copolymers, dimethylsiloxane/methylhydrosiloxane cyclic copolymers, and trimethylsiloxy-terminated dimethylsiloxane/methylhydrosiloxane/laurylmethylsiloxane copolymers.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, in particular polyoxyalkylenes having at least two vinyl groups, reacting with Si—H bonds of a polysiloxane.

The polyoxyalkylenated silicone elastomer according to the invention is preferably mixed with at least one hydrocarbon-based oil and/or one silicone oil to form a gel. In these gels, the polyoxyalkylenated elastomer can be in the form of non-spherical particles.

Polyoxyalkylenated elastomers are described especially in U.S. Pat. Nos. 5,236,986, 5,412,004, 5,837,793 and 5,811,487.

As polyoxyalkylenated silicone elastomers, use may be made of those having the following INCI names:
Dimethicone/PEG-10/15-Crosspolymer,
PEG-15/Lauryl Dimethicone Crosspolymer,
PEG-10/Lauryl Dimethicone Crosspolymer,
PEG-12 Dimethicone Crosspolymer,
PEG-10 Dimethicone Crosspolymer,
PEG-10 Dimethicone/Vinyl Dimethicone Crosspolymer,
PEG-12 Dimethicone/PPG-20 Crosspolymer,
and mixtures thereof.

They are especially sold under the KSG® names by Shin Etsu:
KSG-210® (INCI name: Dimethicone and Dimethicone/PEG-10/15-Crosspolymer;
KSG-310® (INCI name: PEG-15/Lauryl Dimethicone Crosspolymer and Mineral oil;
KSG-320® (INCI name: PEG-15/Lauryl Dimethicone Crosspolymer and Isododecane;
KSG-330® (INCI name: PEG-15/Lauryl Dimethicone Crosspolymer and Triethylhexanoin;

KSG-340® (INCI name: Squalane and PEG-15/Lauryl Dimethicone Crosspolymer.

They are especially sold by Dow Corning under the name Dow Corning 9011 Silicone Elastomer Blend®; INCI name: Cyclopentasiloxane and PEG-12 Dimethicone Crosspolymer.

Mention may also be made of the product sold under the name Dow Corning EL-7040 Hydro Elastomer Blend® by Dow Corning for the compound which has the INCI name: PEG-12 Dimethicone/PPG-20 Crosspolymer.

b) Polyglycerolated Silicone Elastomers

The polyglycerolated silicone elastomer is an elastomeric crosslinked organopolysiloxane that may be obtained by a crosslinking addition reaction of diorganopolysiloxane containing at least one hydrogen bonded to the silicon and of polyglycerolated compounds having ethylenically unsaturated groups, especially in the presence of a platinum catalyst.

Preferably, the elastomeric crosslinked organopolysiloxane is obtained by a crosslinking addition reaction (A) of diorganopolysiloxane containing at least two hydrogens each bonded to a silicon, and (B) of glycerolated compounds having at least two ethylenically unsaturated groups, especially in the presence (C) of a platinum catalyst.

In particular, the organopolysiloxane may be obtained by reaction of a dimethylvinylsiloxy-terminated polyglycerolated compound and of trimethylsiloxy-terminated methylhydropolysiloxane, in the presence of a platinum catalyst.

Compound (A) is the base reagent for the formation of organopolysiloxane elastomer, and the crosslinking is performed by addition reaction of compound (A) with compound (B) in the presence of catalyst (C).

Compound (A) is in particular an organopolysiloxane having at least two hydrogen atoms bonded to separate silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be readily miscible with compound (B).

The organic groups bonded to the silicon atoms of compound (A) may be alkyl groups having from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3, 3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Preferably, said organic group is chosen from methyl, phenyl and lauryl groups.

Compound (A) may thus be chosen from trimethylsiloxy-terminated methylhydropolysiloxanes, trimethylsiloxy-terminated dimethylsiloxane/methylhydrosiloxane copolymers, dimethylsiloxane/methylhydrosiloxane cyclic copolymers, and trimethylsiloxy-terminated dimethylsiloxane/methylhydrosiloxane/laurylmethylsiloxane copolymers.

Compound (B) may be a polyglycerolated compound corresponding to the formula (B') below:

$$C_mH_{2m-1}\text{—O-[Gly]}_n\text{-}C_mH_{2m-1} \tag{B'}$$

in which m is an integer ranging from 2 to 6, n is an integer ranging from 2 to 200, preferably ranging from 2 to 100, preferably ranging from 2 to 50, preferably n ranging from 2 to 20, preferably ranging from 2 to 10 and preferentially ranging from 2 to 5, and in particular n is equal to 3; Gly denotes:

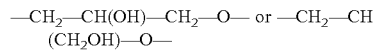

Advantageously, the sum of the number of ethylenic groups per molecule of compound (B) and of the number of hydrogen atoms bonded to silicon atoms per molecule of compound (A) is at least 4.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

The polyglycerolated silicone elastomer according to the invention is generally mixed with at least one hydrocarbon-based oil and/or one silicone oil to form a gel. In these gels, the polyglycerolated elastomer is often in the form of non-spherical particles.

Such elastomers are described especially in patent application WO 2004/024798.

Use may be made, as polyglycerolated silicone elastomers, of the following compounds having the INCI name:
Dimethicone/Polyglycerin-3 Crosspolymer,
Lauryl Dimethicone/Polyglycerin-3 Crosspolymer,
and mixtures thereof.

They are especially sold by Shin Etsu under the following names:
KSG-710®; INCI name: Dimethicone/Polyglycerin-3 Crosspolymer and Dimethicone;
KSG-810®; INCI name: Mineral Oil and Lauryl Dimethicone/Polyglycerin-3 Crosspolymer;
KSG-820®; INCI name: Isododecane and Lauryl Dimethicone/Polyglycerin-3 Crosspolymer;
KSG-830®; INCI name: Triethylhexanoin and Lauryl Dimethicone/Polyglycerin-3 Crosspolymer;
KSG-840®; INCI name: Squalane and Lauryl Dimethicone/Polyglycerin-3 Crosspolymer.

According to one particular form of the invention, the following will be chosen as emulsifiers:
PEG-30 Dipolyhydroxystearate;
and Polyglyceryl-4 Diisostearate/Polyhydroxystearate/Sebacate;
and mixtures thereof.

Additives

The compositions according to the invention can in addition comprise additives commonly used in care and/or makeup products, such as
active agents such as vitamins, for example vitamins A, E and C; moisturizers;
sunscreens,
pigments,
fillers,
water-soluble colorants and/or liposoluble colorants;
and mixtures thereof.

It is a matter of routine operation for those skilled in the art to adjust the nature and the amount of the additives present in the compositions in accordance with the invention such that the desired cosmetic properties thereof are not thereby affected.

UV-Screening Agents

The compositions according to the invention may also contain one or more UV-screening agents chosen from organic UV-screening agents and/or inorganic screening agents.

i) Organic UV-Screening Agents

The organic UV-screening agents are especially chosen from cinnamic compounds; diphenylacrylate compounds; salicylate compounds; dibenzoylmethane compounds; anthranilate compounds; benzylidenecamphor compounds; benzophenone compounds; triazine compounds; benzotriazole compounds, especially the silicone benzotriazoles described in patent EP0392883 and the methylenebis(hydroxyphenyl benzotriazole) compounds as described in applications U.S. Pat. Nos. 5,237,071, 5,166355, GB2303549, DE 197 26 184 and EP893119; benzalmalonate compounds, especially those mentioned in patent U.S. Pat. No. 5,624,663; benzimidazole compounds; imidazoline compounds; the bis-benzoazolyl compounds as described in patents EP669323 and U.S. Pat. No. 2,463,264; benzoxazole compounds as described in patent applications EP0832642, EP1027883, EP1300137 and DE10162844; screening polymers and screening silicones such as those described especially in application WO-93/04665; merocyanine compounds as described in patent U.S. Pat. No. 4,195,999, application WO2004/006878, applications WO2008/090066, WO2011113718, WO2009027258, WO2013010590, WO2013011094, WO2013011480 and the documents IP COM JOURNAL No 000179675D published on 23 Feb. 2009, IP COM JOURNAL No 000182396D published on 29 Apr. 2009, IP COM JOURNAL No 000189542D published on 12 Nov. 2009, and IP COM Journal No IPCOM000011179D published on Apr. 3, 2004, and mixtures thereof.

As examples of organic photoprotective agents, mention may be made of those denoted hereinbelow under their INCI name:

Dibenzoylmethane Compounds

Butyl methoxydibenzoylmethane sold especially under the trade name Parsol 1789 by DSM Nutritional Products, Inc.;

Cinnamic Compounds:

Ethylhexyl methoxycinnamate, sold especially under the trade name Parsol MCX® by DSM Nutritional Products, Isopropyl methoxycinnamate, Isoamyl p-methoxycinnamate sold under the trade name Neo Heliopan E 1000® by Symrise.

Salicylic Compounds:

Homosalate, sold under the name Eusolex HMSO by Rona/EM Industries, Ethylhexyl salicylate, sold under the name Neo Heliopan OS® by Symrise, Dipropylene glycol salicylate, sold under the name Dipsal® by Scher, TEA salicylate, sold under the name Neo Heliopan TS® by Symrise.

β,β-Diphenylacrylate Compounds:

Octocrylene, sold especially under the trade name Uvinul N 539® by BASF, Etocrylene, sold especially under the trade name Uvinul N 35® by BASF.

Benzophenone Compounds:

Benzophenone-1 sold under the trade name Uvinul 400® by BASF,

Benzophenone-2, sold under the trade name Uvinul D 50® by BASF,

Benzophenone-3 or Oxybenzone, sold under the trade name Uvinul M 40® by BASF,

Benzophenone-4, sold under the trade name Uvinul MS 40® by BASF,

Benzophenone-5,

Benzophenone-6 sold under the trade name Helisorb 11® by Norquay,

Benzophenone-8, sold under the trade name Spectra-Sorb UV-24® by American Cyanamid, Benzophenone-9, sold under the trade name Uvinul DS 49® by BASF, Benzophenone-12, n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by BASF, 1,1'-(1,4-Piperazinediyl)bis[1-[2-[4-(diethylamino)-2-hydroxybenzoyl]phenyl]methanone] (CAS 919803-06-8), as described in patent application WO 2007/071 584; this compound advantageously being used in micronized form (mean size of 0.02 to 2 µm), which may be obtained, for example, according to the micronization process described in patent applications GB-A-2 303 549 and EP-A-893 119, and especially in the form of an aqueous dispersion.

Benzylidenecamphor Compounds:

3-Benzylidenecamphor, manufactured under the name Mexoryl SD® by Chimex,

4-Methylbenzylidenecamphor, sold under the name Eusolex 6300® by Merck,

Benzylidenecamphorsulfonic acid, manufactured under the name Mexoryl SL® by Chimex, Camphor benzalkonium methosulfate, manufactured under the name Mexoryl SO® by Chimex, Terephthalylidenedicamphorsulfonic acid, manufactured under the name Mexoryl SX® by Chimex, Polyacrylamidomethylbenzylidenecamphor, manufactured under the name Mexoryl SW® by Chimex.

Phenylbenzimidazole Compounds:

Phenylbenzimidazolesulfonic acid, sold in particular under the trade name Eusolex 232® by Merck.

Bis-benzoazolyl Compounds

Disodium phenyl dibenzimidazole tetrasulfonate, sold under the trade name Neo Heliopan AP by Symrise.

Benzotriazole Compounds

Drometrizole trisiloxane, manufactured under the name Mexoryl SX® by Chimex. Methylene bis-benzotriazolyl tetramethylbutylphenol in particular in solid form, such as the product sold under the trade name MIXXIM BB/100® by Fairmount Chemical or in the form of an aqueous dispersion of micronized particles having a mean particle size which ranges from 0.01 to 5 µm and more preferentially from 0.01 to 2 µm and more particularly from 0.020 to 2 µm, with at least one alkylpolyglycoside surfactant of structure:

$C_nH_{2n+1}O(C_6H_{10}O_5)_xH$ in which n is an integer from 8 to 16 and x is the average degree of polymerization of the $(C_6H_{10}O_5)$ unit and ranges from 1.4 to 1.6, as described in patent GB-A-2 303 549, especially sold under the trade name Tinosorb M® by BASF or in the form of an aqueous dispersion of micronized particles having a mean particle size which ranges from 0.02 to 2 µm and more preferentially from 0.01 to 1.5 µm and more particularly from 0.02 to 1 µm in the presence of at least one mono-($C_8$-$C_{20}$)alkyl ester of polyglycerol having a degree of glycerol polymerization of at least 5, such as the aqueous dispersions described in application WO2009/063392.

Triazine Compounds:

Bis-Ethylhexyloxyphenol methoxyphenyl triazine, sold under the trade name Tinosorb S® by BASF, Ethylhexyl triazone, sold in particular under the trade name Uvinul T150® by BASF, Diethylhexyl butamido triazone, sold under the trade name Uvasorb HEB® by Sigma 3V, symmetrical triazine screening agents substituted with naphthalenyl groups or polyphenyl groups described in U.S. Pat. No. 6,225,467, patent application WO 2004/085 412 (see compounds 6 and 9) or the document "Symmetrical Triazine Derivatives", IP.COM IPCOM000031257 Journal, INC, West Henrietta, N.Y., US (20 Sep. 2004), especially 2,4,6-tris(diphenyl)triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 µm), which may be obtained, for example, according to the micronization process described in patent applications GB-A-2 303 549 and EP-A-893 119, and especially in aqueous dispersion;

silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy] disiloxanyl}propyl)amino]-s-triazine.

Anthranilic Compounds:

Menthyl anthranilate, sold under the trade name Neo Heliopan MA® by Symrise.

Imidazoline Compounds:

Ethylhexyl dimethoxybenzylidene dioxoimidazoline propionate.

Benzalmalonate Compounds:

Polyorganosiloxane containing benzalmalonate functional groups, for instance Polysilicone-15, sold under the trade name Parsol SLX® by DSM Nutritional Products, Inc.

Benzoxazole Compounds:

2,4-bis[5-1(dimethylpropyl)benzoxazol-2-yl(4-phenyl)imino]-6-(2-ethylhexyl)imino-1,3,5-triazine, sold under the name Uvasorb K2A® by Sigma 3V.

ii) Inorganic UV Screening Agents

The inorganic UV-screening agents used in accordance with the present invention are metal oxide pigments. More preferentially, the inorganic UV-screening agents of the invention are metal oxide particles with an average elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be chosen especially from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil® from Ikeda, with silica and iron oxide, such as the product Sunveil F® from Ikeda, with silica and alumina, such as the products Microtitanium Dioxide MT 500 SA® and Microtitanium Dioxide MT 100 SA from Tayca and Tioveil from Tioxide, with alumina, such as the products Tipaque TTO-55 (B)® and Tipaque TTO-55 (A)® from Ishihara and UVT 14/4 from Sachtleben Pigments, with alumina and aluminium stearate, such as the products Microtitanium Dioxide MT 100 T®, MT 100 TX®, MT 100 Z® and MT-01® from Tayca, the products Solaveil CT-10 W® and Solaveil CT 100® from Uniqema and the product Eusolex T-AVO® from Merck, with silica, alumina and alginic acid, such as the product MT-100 AQ® from Tayca, with alumina and aluminium laurate, such as the product Microtitanium Dioxide MT 100 S® from Tayca, with iron oxide and iron stearate, such as the product Microtitanium Dioxide MT 100 F® from Tayca, with zinc oxide and zinc stearate, such as the product BR 351® from Tayca, with silica and alumina and treated with a silicone, such as the products Microtitanium Dioxide MT 600 SAS®, Microtitanium Dioxide MT 500 SAS® or Microtitanium Dioxide MT 100 SAS® from Tayca, with silica, alumina and aluminium stearate and treated with a silicone, such as the product STT-30-DS® from Titan Kogyo, with silica and treated with a silicone, such as the product UV-Titan X 195® from Sachtleben Pigments, with alumina and treated with a silicone, such as the products Tipaque TTO-55 (S)® from Ishihara or UV Titan M 262® from Sachtleben Pigments, with triethanolamine, such as the product STT-65-S from Titan Kogyo, with stearic acid, such as the product Tipaque TTO-55 (C)® from Ishihara, with sodium hexametaphosphate, such as the product Microtitanium Dioxide MT 150 W® from Tayca, $TiO_2$ treated with octyltrimethylsilane, sold under the trade name T 805® by Degussa Silices, $TiO_2$ treated with a polydimethylsiloxane, sold under the trade name 70250 Cardre UF TiO2SI3® by Cardre, anatase/rutile $TiO_2$ treated with a polydimethylhydrogenosiloxane, sold under the trade name Microtitanium Dioxide USP Grade Hydrophobic® by Color Techniques.

Mention may also be made of $TiO_2$ pigments doped with at least one transition metal such as iron, zinc or manganese and more particularly manganese. Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of TiO₂ particles doped with manganese in capric/caprylic acid triglyceride in the presence of TRI-PPG-3 myristyl ether citrate and polyglyceryl-3 polyricinoleate and sorbitan isostearate having the INCI name: Titanium dioxide (and) TRI-PPG-3 myristyl ether citrate (and) polyglyceryl-3 ricinoleate (and) sorbitan isostearate, for instance the product sold under the trade name Optisol TD50® by Croda.

The uncoated titanium oxide pigments are sold, for example, by Tayca under the trade names Microtitanium Dioxide MT 500 B or Microtitanium Dioxide MT 600 B®, by Degussa under the name P 25, by Wackherr under the name Transparent titanium oxide PW®, by Miyoshi Kasei under the name UFTRO, by Tomen under the name ITS® and by Tioxide under the name Tioveil AQ.

The uncoated zinc oxide pigments are for example:
those sold under the name Z-Cote by Sunsmart;
those sold under the name Nanox® by Elementis;
those sold under the name Nanogard WCD 2025® by Nanophase Technologies.

The coated zinc oxide pigments are for example:
those sold under the name Zinc Oxide CS-5® by Toshibi (ZnO coated with polymethylhydrogenosiloxane);
those sold under the name Nanogard Zinc Oxide FN® by Nanophase Technologies (as a 40% dispersion in Finsolv TN®, C12-C15 alkyl benzoate);
those sold under the name Daitopersion Zn-30® and Daitopersion Zn-50® by Daito (dispersions in cyclopolymethylsiloxane/oxyethylenated polydimethylsiloxane, containing 30% or 50% of zinc oxides coated with silica and polymethylhydrogenosiloxane);
those sold under the name NFD Ultrafine ZnO® by Daikin (ZnO coated with perfluoroalkyl phosphate and copolymer based on perfluoroalkylethyl as a dispersion in cyclopentasiloxane);
those sold under the name SPD-Z1® by Shin-Etsu (ZnO coated with silicone-grafted acrylic polymer, dispersed in cyclodimethylsiloxane);
those sold under the name Escalol Z100® by ISP (alumina-treated ZnO dispersed in the ethylhexyl methoxycinnamate/PVP-hexadecene copolymer/methicone mixture);
those sold under the name Fuji ZnO-SMS-10® by Fuji Pigment (ZnO coated with silica and polymethylsilsesquioxane);
those sold under the name Nanox Gel TN® by Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by Rhône-Poulenc.

The uncoated iron oxide pigments are sold, for example, by Arnaud under the names Nanogard WCD 2002® (FE 45B®), Nanogard Iron FE 45 BL AQ, Nanogard FE 45R AQ® and Nanogard WCD 2006® (FE 45R®) or by Mitsubishi under the name TY-220®.

The coated iron oxide pigments are sold, for example, by Arnaud under the names Nanogard WCD 2008 (FE 45B FN)®, Nanogard WCD 2009® (FE 45B 556®), Nanogard FE 45 BL 345® and Nanogard FE 45 BL® or by BASF under the name Transparent Iron Oxide®.

Mention may also be made of mixtures of metal oxides, especially of titanium dioxide and of cerium dioxide, including the equal-weight mixture of titanium dioxide and cerium dioxide coated with silica, sold by Ikeda under the name Sunveil A®, and also the mixture of titanium dioxide and zinc dioxide coated with alumina, silica and silicone, such as the product M 261® sold by Sachtleben Pigments, or coated with alumina, silica and glycerol, such as the product M 211® sold by Sachtleben Pigments.

According to the invention, the coated or uncoated inorganic screening agents based on titanium oxide are particularly preferred.

The UV-screening agents according to the invention are preferably present in the compositions according to the invention in a content ranging from 0.1% to 45% by weight and in particular from 5% to 30% by weight relative to the total weight of the composition.

Pigments

According to one particular embodiment of the invention, the composition according to the invention comprises at least one pigment.

The term "pigments" is intended to mean white or coloured, mineral or organic particles, which are insoluble in an aqueous medium, and which are intended to colour and/or opacify the resulting composition and/or deposit. These pigments may be white or coloured, and mineral and/or organic.

Preferably, the composition comprises at least 5% by weight of pigments, more preferentially from 5% to 40% by weight of pigments, in particular from 10% to 30% by weight and preferably from 10% to 20% by weight of pigments, relative to the total weight of said composition.

According to a particular embodiment, the pigments used according to the invention are chosen from mineral pigments.

The term "mineral pigment" is intended to mean any pigment that satisfies the definition in Ullmann's encyclopaedia in the chapter on inorganic pigments. Among the mineral pigments that are useful in the present invention, mention may be made of zirconium oxide or cerium oxide, and also zinc oxide, iron oxide (black, yellow or red) or chromium oxide, manganese violet, ultramarine blue, chromium hydrate and ferric blue, titanium dioxide, and metal powders, for instance aluminium powder or copper powder. The following mineral pigments may also be used: $Ta_2O_5$, $Ti_3O_5$, $Ti_2O_3$, TiO, $ZrO_2$ as a mixture with $TiO_2$, $ZrO_2$, $Nb_2O_5$, $CeO_2$, ZnS.

The size of the pigment that is useful in the context of the present invention is generally greater than 100 nm and can range up to 10 μm, preferably from 200 nm to 5 μm and more preferentially from 300 nm to 1 μm.

According to one particular form of the invention, the pigments have a size characterized by a D[50] greater than 100 nm and possibly ranging up to 10 μm, preferably from 200 nm to 5 μm and more preferentially from 300 nm to 1 μm.

The sizes are measured by static light scattering using a commercial MasterSizer 3000 particle size analyser from Malvern, which makes it possible to determine the particle size distribution of all of the particles over a wide range which may extend from 0.01 μm to 1000 μm. The data are processed on the basis of the standard Mie scattering theory. This theory is the most suitable for size distributions ranging from submicron to multimicron; it allows an "effective" particle diameter to be determined. This theory is described especially in the publication by Van de Hulst, H. C., Light Scattering by Small Particles, Chapters 9 and 10, Wiley, New York, 1957.

D[50] represents the maximum size that 50% by volume of the particles have.

In the context of the present invention, the mineral pigments are more particularly iron oxide and/or titanium dioxide. By way of example, mention may more particularly be made of titanium dioxides and iron oxide coated with aluminium stearoyl glutamate, sold, for example, under the reference NAI by Miyoshi Kasei.

As inorganic pigments of use in the invention, mention may be made of pearlescent agents.

The term "pearlescent agents" should be understood as meaning coloured particles of any shape, which are or are not iridescent, especially produced by certain mollusks in their shells or else synthesized, and which exhibit a colour effect via optical interference.

The pearlescent agents may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic colorants.

Examples of pearlescent agents that may also be mentioned include natural mica covered with titanium oxide, with iron oxide, with natural pigment or with bismuth oxychloride.

Among the pearlescent agents available on the market, mention may be made of the pearlescent agents Timica, Flamenco and Duochrome (based on mica) sold by Engelhard, the Timiron pearlescent agents sold by Merck, the Prestige mica-based pearlescent agents sold by Eckart, and the Sunshine synthetic mica-based pearlescent agents sold by Sun Chemical.

The pearlescent agents may more particularly have a yellow, pink, red, bronze, orangey, brown, gold and/or coppery colour or glint.

By way of illustration of pearlescent agents which can be used in the context of the present invention, mention may especially be made of pearlescent agents of gold colour sold especially by Engelhard under the names Brilliant Gold 212G (Timica), Gold 222C (Cloisonne), Sparkle Gold (Timica), Gold 4504 (Chromalite) and Monarch Gold 233X (Cloisonne); bronze pearlescent agents sold especially by Merck under the names Bronze Fine (17384) (Colorona) and Bronze (17353) (Colorona) and by Engelhard under the name Super Bronze (Cloisonne); orange pearlescent agents sold especially by Engelhard under the names Orange 363C (Cloisonne) and Orange MCR 101 (Cosmica) and by Merck under the names Passion Orange (Colorona) and Matte Orange (17449) (Microna); brown-coloured pearlescent agents sold especially by Engelhard under the names Nu-Antique Copper 340XB (Cloisonne) and Brown CL4509 (Chromalite); pearlescent agents with a copper glint sold especially by Engelhard under the name Copper 340A (Timica); pearlescent agents with a red glint sold especially by Merck under the name Sienna Fine (17386) (Colorona); pearlescent agents with a yellow glint sold especially by Engelhard under the name Yellow (4502) (Chromalite); red-coloured pearlescent agents with a gold glint sold especially by Engelhard under the name Sunstone G012 (Gemtone); pink pearlescent agents sold especially by Engelhard under the name Tan Opale G005 (Gemtone); black pearlescent agents with a gold glint sold especially by Engelhard under the name Nu-Antique Bronze 240 AB (Timica); blue pearlescent agents sold especially by Merck under the name Matte Blue (17433) (Microna); white pearlescent agents with a silvery glint sold especially by Merck under the name Xirona Silver; and golden green pinkish orangey pearlescent agents sold especially by Merck under the name Indian Summer (Xirona), and mixtures thereof.

Among the pigments of use according to the invention, mention may be made of those having an optical effect different from a simple conventional colouring effect, that is to say a unified and stabilized effect such as produced by conventional colourants, such as, for example, monochromatic pigments. Within the meaning of the invention, the term "stabilized" means devoid of an effect of variability in the colour with the angle of observation or alternatively in response to a change in temperature.

For example, this material can be chosen from particles with a metallic glint, goniochromatic colouring agents, diffracting pigments, thermochromic agents, optical brighteners and also fibres, especially interference fibres. Of course, these various materials can be combined so as to provide the simultaneous display of two effects, indeed even of a novel effect in accordance with the invention.

The particles with a metallic glint of use in the invention are in particular chosen from:
particles of at least one metal and/or of at least one metal derivative,
particles comprising a monomaterial or multimaterial organic or mineral substrate, at least partially coated with at least one layer with a metallic glint comprising at least one metal and/or at least one metal derivative; and
mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo, Cr and mixtures or alloys thereof (for example, bronzes and brasses) are preferred metals.

The term "metal derivatives" denotes compounds derived from metals, in particular oxides, fluorides, chlorides and sulfides.

Mention may be made, by way of illustration of these particles, of aluminium particles, such as those sold under the names Starbrite 1200 EAC® by Silberline and Metalure® by Eckart.

Mention may also be made of metal powders formed of copper or alloy mixtures, such as the references 2844 sold by Radium Bronze, metal pigments, such as aluminium or bronze, for example those sold under the names Rotosafe 700 from Eckart, silica-coated aluminium particles sold under the name Visionaire Bright Silver from Eckart and particles formed of metal alloy, such as powders formed of bronze (copper and zinc alloy) coated with silica sold under the name Visionaire Bright Natural Gold from Eckart.

The particles can also comprise a glass substrate, such as those sold by Nippon Sheet Glass under the names Microglass Metashine.

The goniochromatic colouring agent can be chosen, for example, from interference multilayer structures and liquid crystal colouring agents.

Examples of symmetrical interference multilayer structures which can be used in compositions produced in accordance with the invention are, for example, the following structures: $Al/SiO_2/Al/SiO_2/Al$, pigments having this structure being sold by DuPont de Nemours; $Cr/MgF_2/Al/MgF_2/Cr$, pigments having this structure being sold under the name Chromaflair by Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by BASF; $MoS_2/SiO_2/$mica-oxide/$SiO_2/MoS_2$; $Fe_2O_3/SiO_2/$mica-oxide/$SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/$mica$/TiO_2/SiO_2/TiO_2/$mica$/SnO$, pigments having these structures being sold under the name Xirona by Merck (Darmstadt). By way of example, these pigments can be pigments with a silica/titanium oxide/tin oxide structure sold under the name Xirona Magic by Merck, pigments with a silica/brown iron oxide structure sold under the name Xirona Indian Summer by Merck and pigments with a silica/titanium oxide/mica/tin oxide structure sold under the name Xirona Caribbean Blue by Merck. Mention may also be made of the Infinite Colors pigments from Shiseido. Different effects are obtained according to the thickness and the nature of the various layers. Thus, with the $Fe_2O_3/SiO_2/Al/SiO_2/Fe_2O_3$ structure, the colour changes from greenish gold to reddish grey for $SiO_2$ layers of 320 to 350 nm; from red to gold for $SiO_2$ layers of 380 to 400 nm; from violet to green for $SiO_2$ layers of 410 to 420 nm; from copper to red for $SiO_2$ layers of 430 to 440 nm.

Mention may be made, as examples of pigments with a polymeric multilayer structure, of those sold by 3M under the name Color Glitter.

Use may be made, as liquid crystal goniochromatic particles, for example, of those sold by Chenix and of that sold under the name Helicone® HC by Wacker.

Hydrophobic Coated Pigments

Preferably, the compositions according to the invention comprise at least one pigment coated with at least one lipophilic or hydrophobic compound and especially as detailed below.

This type of pigment is particularly advantageous insofar as it may be considered in large amount together with a large amount of water. What is more, insofar as they are treated with a hydrophobic compound, they show a predominant affinity for the oily gelled phase, which can then convey them.

Needless to say, the compositions according to the invention may in parallel contain uncoated pigments.

The coating may also comprise at least one additional non-lipophilic compound. For the purposes of the invention, the "coating" of a pigment according to the invention generally denotes the total or partial surface treatment of the pigment with a surface agent, absorbed, adsorbed or grafted onto said pigment.

The surface-treated pigments may be prepared according to surface treatment techniques of chemical, electronic, mechanochemical or mechanical nature that are well known to those skilled in the art. Commercial products may also be used.

The surface agent may be absorbed, adsorbed or grafted onto the pigments by evaporation of solvent, chemical reaction and creation of a covalent bond.

According to one variant, the surface treatment is constituted of a coating of the pigments.

The coating may represent from 0.1% to 20% by weight and in particular from 0.5% to 5% by weight, of the total weight of the coated pigment.

The coating may be performed, for example, by adsorption of a liquid surface agent onto the surface of the solid particles by simple mixing with stirring of the particles and of said surface agent, optionally with heating, prior to the incorporation of the particles into the other ingredients of the makeup or care composition.

The coating may be performed, for example, by chemical reaction of a surface agent with the surface of the solid pigment particles and creation of a covalent bond between the surface agent and the particles. This method is especially described in U.S. Pat. No. 4,578,266.

The chemical surface treatment may consist in diluting the surface agent in a volatile solvent, dispersing the pigments in this mixture and then slowly evaporating off the volatile solvent, so that the surface agent is deposited at the surface of the pigments.

Lipophilic or Hydrophobic Treatment Agent

When the pigment comprises a lipophilic or hydrophobic coating, the latter is preferably present in the fatty phase of the composition according to the invention.

According to a particular embodiment of the invention, the pigments may be coated according to the invention with at least one compound chosen from silicone surface agents; fluoro surface agents; fluorosilicone surface agents; metal soaps; N-acylamino acids or salts thereof; lecithin and derivatives thereof; isopropyl triisostearyl titanate; isostearyl sebacate; natural plant or animal waxes; polar synthetic waxes; fatty esters; phospholipids; and mixtures thereof.

Silicone Surface Agent

According to a particular embodiment, the pigments may be totally or partially surface-treated with a compound of silicone nature.

The silicone surface agents may be chosen from organopolysiloxanes, silane derivatives, silicone-acrylate copolymers, silicone resins, and mixtures thereof.

The term "organopolysiloxane compound" means a compound having a structure comprising an alternance of silicon atoms and oxygen atoms and comprising organic radicals linked to silicon atoms.

Non-Elastomeric Organopolysiloxane

Non-elastomeric organopolysiloxanes that may especially be mentioned include polydimethylsiloxanes, polymethylhydrogenosiloxanes and polyalkoxydimethylsiloxanes.

The alkoxy group may be represented by the radical R—O— such that R represents methyl, ethyl, propyl, butyl or octyl, 2-phenylethyl, 2-phenylpropyl or 3,3,3-trifluoropropyl radicals, aryl radicals such as phenyl, tolyl or xylyl, or substituted aryl radicals such as phenylethyl.

One method which makes it possible to surface-treat pigments with a polymethylhydrogenosiloxane consists in dispersing the pigments in an organic solvent and then in adding the silicone compound. On heating the mixture, covalent bonds are created between the silicone compound and the surface of the pigment.

According to one preferred embodiment, the silicone surface agent may be a non-elastomeric organopolysiloxane, especially chosen from polydimethylsiloxanes.

Alkylsilanes and Alkoxysilanes

Silanes containing alkoxy functionality are especially described by Witucki in "A silane primer, chemistry and applications of alkoxy silanes", Journal of Coatings Technology, 65, 822, pages 57-60, 1993.

Alkoxysilanes such as the alkyltriethoxysilanes and the alkyltrimethoxysilanes sold under the references Silquest A-137 (OSI Specialities) and Prosil 9202 (PCR) may be used for coating the pigments.

The use of alkylpolysiloxanes bearing a reactive end group such as alkoxy, hydroxyl, halogen, amino or imino is described in patent application JP H07-196946. They are also suitable for treating the pigments.

Silicone-Acrylate Polymers

Grafted silicone-acrylic polymers having a silicone backbone as described in U.S. Pat. Nos. 5,725,882, 5,209,924, 4,972,037, 4,981,903, 4,981,902 and 5,468,477 and in U.S. Pat. No. 5,219,560 and EP 0 388 582 may be used.

Other silicone-acrylate polymers may be silicone polymers comprising in their structure the unit of formula (I) below:

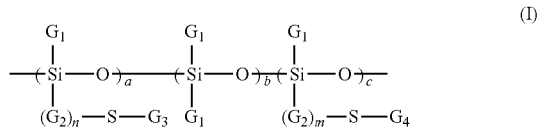

in which the radicals $G_1$, which may be identical or different, represent hydrogen or a $C_1$-$C_{10}$ alkyl radical or alternatively a phenyl radical; the radicals $G_2$, which may be identical or different, represent a $C_1$-$C_{10}$ alkylene group; $G_3$ represents a polymeric residue resulting from the (homo)polymerization of at least one ethylenically unsaturated anionic monomer; $G_4$ represents a polymeric residue resulting from the (homo)polymerization of at least one ethylenically unsaturated hydrophobic monomer; m and n are equal to 0 or 1; a is an integer ranging from 0 to 50; b is an integer that may be between 10 and 350, c is an integer ranging from 0 to 50; with the proviso that one of the parameters a and c is other than 0.

Preferably, the unit of formula (I) above has at least one, and even more preferentially all, of the following characteristics:

the radicals $G_1$ denote an alkyl radical, preferably the methyl radical;

n is non-zero, and the radicals $G_2$ represent a divalent $C_1$-$C_3$ radical, preferably a propylene radical;

$G_3$ represents a polymeric radical resulting from the (homo)polymerization of at least one monomer of the ethylenically unsaturated carboxylic acid type, preferably acrylic acid and/or methacrylic acid;

$G_4$ represents a polymeric radical resulting from the (homo)polymerization of at least one monomer of the ($C_1$-$C_{10}$)alkyl (meth)acrylate type, preferably such as isobutyl or methyl (meth)acrylate.

Examples of silicone polymers corresponding to formula (I) are especially polydimethylsiloxanes (PDMS) onto which are grafted, via a connecting chain unit of thiopropylene type, mixed polymer units of the poly(meth)acrylic acid type and of the polymethyl (meth)acrylate type.

Other examples of silicone polymers corresponding to formula (I) are especially polydimethylsiloxanes (PDMS) onto which are grafted, via a connecting chain unit of thiopropylene type, polymer units of the polyisobutyl (meth)acrylate type.

Silicone Resins

The silicone surface agent may be chosen from silicone resins.

The term "resin" means a three-dimensional structure.

The silicone resins may be soluble or swellable in silicone oils. These resins are crosslinked polyorganosiloxane polymers.

The nomenclature of silicone resins is known under the name "MDTQ", the resin being described as a function of the various siloxane monomer units that it comprises, each of the letters "MDTQ" characterizing a type of unit.

The letter M represents the monofunctional unit of formula $(CH_3)_3SiO_{1/2}$, the silicon atom being connected to only one oxygen atom in the polymer comprising this unit.

The letter D means a difunctional unit $(CH_3)_2SiO_{2/2}$ in which the silicon atom is bonded to two oxygen atoms.

The letter T represents a trifunctional unit of formula $(CH_3)SiO_{3/2}$.

In the units M, D and T defined above, at least one of the methyl groups may be substituted with a group R other than a methyl group, such as a hydrocarbon-based radical (especially alkyl) having from 2 to 10 carbon atoms or a phenyl group, or alternatively a hydroxyl group.

Finally, the letter Q means a tetrafunctional unit $SiO_{4/2}$ in which the silicon atom is bonded to four hydrogen atoms, which are themselves bonded to the rest of the polymer.

Various resins with different properties may be obtained from these different units, the properties of these polymers varying as a function of the type of monomers (or units), of the type and number of substituted radicals, of the length of the polymer chain, of the degree of branching and of the size of the side chains.

Examples of these silicone resins that may be mentioned include:

siloxysilicates, which may be trimethyl siloxysilicates of formula $[(CH_3)_3XSiXO]_xX(SiO_{4/2})_y$, (MQ units) in which x and y are integers ranging from 50 to 80;

polysilsesquioxanes of formula $(CH_3SiO_{3/2})_x$ (units T) in which x is greater than 100 and at least one of the methyl radicals of which may be substituted with a group R as defined above;

polymethylsilsesquioxanes, which are polysilsesquioxanes in which none of the methyl radicals is substituted with another group.

Such polymethylsilsesquioxanes are described in document U.S. Pat. No. 5,246,694.

As examples of commercially available polymethylsilsesquioxane resins, mention may be made of those sold:

by Wacker under the reference Resin MK, such as Belsil PMS MK: polymer comprising $CH_3SiO_{3/2}$ repeating units (units T), which may also comprise up to 1 by weight of $(CH_3)_2SiO_{2/2}$ units (units D) and having an average molecular weight of about 10 000, or by Shin-Etsu under the references KR-220L, which are composed of units T of formula $CH_3SiO_{3/2}$ and have Si—OH (silanol) end groups, under the reference KR-242A, which comprise 98% of units T and 2% of dimethyl units D and contain Si—OH end groups, or else under the reference KR-251, comprising 88% of units T and 12% of dimethyl units D and contain Si—OH end groups.

Siloxysilicate resins that may be mentioned include trimethyl siloxysilicate (TMS) resins, optionally in the form of powders. Such resins are sold under the references SR1000, E 1 170-002 or SS 4230, by General Electric or under the references TMS 803, Wacker 803 and 804 by Wacker Silicone Corporation.

Mention may also be made of trimethylsiloxysilicate resins sold in a solvent such as cyclomethicone, sold under the name KF-7312J by Shin-Etsu or DC 749 and DC 593 by Dow Corning.

As examples of commercial references of pigments treated with a silicone compound, mention may be made of:

red iron oxide/dimethicone sold under the reference SA-C 338075-10 by Miyoshi Kasei, and a pigment obtained by treating DC Red 7 with a silicone compound, sold by Coletica under the reference Gransil GCM (which is a mixture of D5 and polysilicone 11)

Fluoro Surface Agent

The pigments may be totally or partially surface-treated with a compound of fluoro nature.

The fluoro surface agents may be chosen from perfluoroalkyl phosphates, perfluoropolyethers, polytetrafluoropolyethylenes (PTFE), perfluoroalkanes, perfluoroalkyl silazanes, polyhexafluoropropylene oxides, and polyorganosiloxanes comprising perfluoroalkyl perfluoropolyether groups.

The term "perfluoroalkyl radical" means an alkyl radical in which all the hydrogen atoms have been replaced with fluorine atoms.

Perfluoropolyethers are especially described in patent application EP 0 486 135, and sold under the trade name Fomblin by Montefluos.

Perfluoroalkyl phosphates are in particular described in application JP H05-86984. The perfluoroalkyl diethanolamine phosphates sold by Asahi Glass under the reference AsahiGuard AG530 may be used.

Among the linear perfluoroalkanes, mention may be made of perfluorocycloalkanes, perfluoro(alkylcycloalkanes), perfluoropolycycloalkanes, aromatic perfluoro hydrocarbons (perfluoroarenes) and hydrocarbon-based perfluoro organic compounds comprising at least one heteroatom.

Among the perfluoroalkanes, mention may be made of the linear alkane series such as perfluorooctane, perfluorononane or perfluorodecane.

Among the perfluorocycloalkanes and perfluoro-(alkylcycloalkanes), mention may be made of perfluorodecalin sold under the name Flutec PP5 GMP by Rhodia, perfluoro (methyldecalin) and perfluoro($C_3$-$C_5$ alkylcyclohexanes) such as perfluoro-(butylcyclohexane).

Among the perfluoropolycycloalkanes, mention may be made of bicyclo[3.3.1]nonane derivatives such as perfluorotrimethylbicyclo[3.3.1]nonane, adamantane derivatives such as perfluorodimethyladamantane, and hydrogenated perfluorophenanthrene derivatives such as tetracosafluorotetradecahydrophenanthrene.

Among the perfluoroarenes, mention may be made of perfluoronaphthalene derivatives, for instance perfluoronaphthalene and perfluoromethyl-1-naphthalene.

As examples of commercial references of pigments treated with a fluoro compound, mention may be made of:

yellow iron oxide/perfluoroalkyl phosphate sold under the reference PF 5 Yellow 601 by Daito Kasei;

red iron oxide/perfluoroalkyl phosphate sold under the reference PF 5 Red R 516L by Daito Kasei;

black iron oxide/perfluoroalkyl phosphate sold under the reference PF 5 Black BL100 by Daito Kasei;

titanium dioxide/perfluoroalkyl phosphate sold under the reference PF 5 TiO2 CR 50 by Daito Kasei, yellow iron oxide/perfluoropolymethyl isopropyl ether sold under the reference Iron oxide yellow BF-25-3 by Toshiki;

DC Red 7/perfluoropolymethyl isopropyl ether sold under the reference D&C Red 7 FHC by Cardre Inc.; and DC Red 6/PTFE sold under the reference T 9506 by Warner-Jenkinson.

Fluorosilicone Surface Agent

The pigments may be totally or partially surface-treated with a compound of fluorosilicone nature.

The fluorosilicone compound may be chosen from perfluoroalkyl dimethicones, perfluoroalkyl silanes and perfluoroalkyl trialkoxysilanes.

Perfluoroalkyl silanes that may be mentioned include the products LP-IT and LP-4T sold by Shin-Etsu Silicone.

The perfluoroalkyl dimethicones may be represented by the following formula:

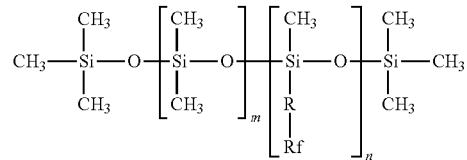

in which:

R represents a linear or branched divalent alkyl group having from 1 to 6 carbon atoms, preferably a divalent methyl, ethyl, propyl or butyl group;

Rf represents a perfluoroalkyl radical having from 1 to 9 carbon atoms and preferably 1 to 4 carbon atoms;

m is chosen between 0 and 150 and preferably from 20 to 100; and n is chosen between 1 and 300 and preferably from 1 to 100.

As examples of commercial references of pigments treated with a fluorosilicone compound, mention may be made of titanium dioxide/fluorosilicone sold under the reference Fluorosil Titanium dioxide 100TA by Advanced Dermaceuticals International Inc.

Other Lipophilic Surface Agents

The hydrophobic treatment agent may also be chosen from:

i) metal soaps such as aluminium dimyristate and the aluminium salt of hydrogenated tallow glutamate.

Metal soaps that may especially be mentioned include metal soaps of fatty acids containing from 12 to 22 carbon atoms and in particular those containing from 12 to 18 carbon atoms.

The metal of the metal soap may especially be zinc or magnesium.

Metal soaps that may be used include zinc laurate, magnesium stearate, magnesium myristate and zinc stearate, and mixtures thereof.

ii) fatty acids such as lauric acid, myristic acid, stearic acid and palmitic acid;

iii) N-acylamino acids or salts thereof, which may comprise an acyl group containing from 8 to 22 carbon atoms, for instance a 2-ethylhexanoyl, caproyl, lauroyl, myristoyl, palmitoyl, stearoyl or cocoyl group.

The amino acid may be, for example, lysine, glutamic acid or alanine.

The salts of these compounds can be the aluminium, magnesium, calcium, zirconium, zinc, sodium or potassium salts.

Thus, according to a particularly preferred embodiment, an N-acylamino acid derivative may especially be a glutamic acid derivative and/or a salt thereof, and more particularly a stearoyl glutamate, for instance aluminium stearoyl glutamate.

iv) lecithin and derivatives thereof;

v) isopropyl triisostearyl titanate.

As examples of isopropyl titanium triisostearate (ITT)-treated pigments, mention may be made of those sold under the commercial references BWBO-I2 (Iron oxide CI77499 and isopropyl titanium triisostearate), BWYO-I2 (Iron oxide CI77492 and isopropyl titanium triisostearate) and BWRO-I2 (Iron oxide CI77491 and isopropyl titanium triisostearate) by Kobo.

vi) isostearyl sebacate;
vii) natural plant or animal waxes or polar synthetic waxes;
viii) fatty esters, in particular jojoba esters;
ix) phospholipids; and
x) mixtures thereof.

The waxes mentioned in the compounds mentioned previously may be those generally used in cosmetics, as defined hereinbelow.

They may especially be hydrocarbon-based, silicone and/or fluoro waxes, optionally comprising ester or hydroxyl functions. They may also be of natural or synthetic origin.

The term "polar wax" means a wax containing chemical compounds comprising at least one polar group. Polar groups are well known to those skilled in the art; they may be, for example, alcohol, ester or carboxylic acid groups. Polyethylene waxes, paraffin waxes, microcrystalline waxes, ozokerite and Fischer-Tropsch waxes are not included among polar waxes.

In particular, the polar waxes have a mean Hansen solubility parameter δa at 25° C. such that δa>0 $(J/cm^3)^{1/2}$ and better still δa>1 $(J/cm^3)^{1/2}$:

$$\delta_a = \sqrt{\delta_p^2 + \delta_h^2}$$

in which δy and δh are, respectively, the polar contributions and contributions of interaction types specific to the Hansen solubility parameters.

The definition of solvents in the three-dimensional solubility space according to Hansen is described in the article by C. M. Hansen: "The three-dimensional solubility parameters", J. Paint Technol. 39, 105 (1967):

δh characterizes the specific interaction forces (such as hydrogen bonding, acid/base, donor/acceptor, etc.);

δy characterizes the Debye interaction forces between permanent dipoles and also the Keesom interaction forces between induced dipoles and permanent dipoles.

The parameters δp and δh are expressed in $(J/cm^3)^{1/2}$.

A polar wax is in particular formed from molecules comprising, besides carbon and hydrogen atoms in their chemical structure, heteroatoms (such as O, N and P).

Non-limiting illustrations of these polar waxes that may in particular be mentioned include natural polar waxes, such as beeswax, lanolin wax, orange wax, lemon wax and Chinese insect waxes, rice bran wax, carnauba wax, candelilla wax, ouricury wax, cork fibre wax, sugarcane wax, Japan wax, sumac wax and montan wax.

According to a particular embodiment, the pigments may be coated with at least one compound chosen from silicone surface agents; fluoro surface agents; N-acylamino acids or salts thereof; isopropyl triisostearyl titanate; natural plant or animal waxes; fatty esters; and mixtures thereof.

According to a particularly preferred embodiment, the pigments may be coated with an N-acylamino acid and/or a salt thereof, in particular with a glutamic acid derivative and/or a salt thereof, or with a fatty ester, in particular with a jojoba ester.

According to a more particularly preferred embodiment, the pigments may be coated with an N-acylamino acid and/or a salt thereof, in particular with a glutamic acid derivative and/or a salt thereof, in particular a stearoyl glutamate, for instance aluminium stearoyl glutamate.

Examples of coated pigments according to the invention that may be mentioned more particularly include titanium dioxides and iron oxide coated with aluminium stearoyl glutamate, sold, for example, under the reference NAI by Miyoshi Kasei.

Pigments not Coated with a Hydrophobic Compound

As stated previously, a composition may also contain pigments not coated with a lipophilic or hydrophobic compound.

These other pigments may be coated with a hydrophilic compound or uncoated.

These pigments may be mineral pigments especially as defined previously.

These pigments may also be organic pigments.

The term "organic pigment" means any pigment that satisfies the definition in Ullmann's encyclopaedia in the chapter on organic pigments. The organic pigment may especially be chosen from nitroso, nitro, azo, xanthene, quinoline, anthraquinone, phthalocyanin, metal complex, isoindolinone, isoindoline, quinacridone, perinone, perylene, diketopyrrolopyrrole, thioindigo, dioxazine, triphenylmethane and quinophthalone compounds.

The organic pigment(s) may be chosen, for example, from carmine, carbon black, aniline black, melanin, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

These pigments may also be in the form of composite pigments as described in patent EP 1 184 426. These composite pigments may especially be composed of particles comprising an inorganic core at least partially covered with an organic pigment and at least one binder for fixing the organic pigments to the core.

The pigment may also be a lake. The term "lake" is intended to mean insolubilized dyes adsorbed onto insoluble particles, the assembly thus obtained remaining insoluble during use.

The inorganic substrates onto which the dyes are adsorbed are, for example, alumina, silica, calcium sodium borosilicate, calcium aluminium borosilicate and aluminium.

Among the organic dyes, mention may be made of cochineal carmine. Mention may also be made of the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

By way of examples of lakes, mention may be made of the product known under the name D&C Red 7 (CI 15 850:1).

Nature of the Hydrophilic Coating

As stated previously, these other pigments may be coated with a hydrophilic compound.

Said hydrophilic compound for surface-treating a pigment in order to optimize its dispersion in the gelled aqueous phase is more particularly chosen from biological polymers, carbohydrates, polysaccharides, polyacrylates and polyethylene glycol derivatives.

As examples of biological polymers, mention may be made of polymers based on monomers of carbohydrate type.

More particularly, mention may be made of biosaccharide gum, chitosans and derivatives thereof, such as butoxy chitosan, carboxymethyl chitosan, carboxybutyl chitosan, chitosan gluconate, chitosan adipate, chitosan glycolate, chitosan lactate, etc., chitins and derivatives thereof, such as carboxymethyl chitin, chitin glycolate; cellulose and derivatives thereof such as cellulose acetate; microcrystalline cellulose; distarch phosphate; sodium hyaluronate; soluble proteoglycans; galacto-arabinans; glycosaminoglycans; glycogen; sclerotium gum; dextran; starch and derivatives thereof; and mixtures thereof.

As examples of carbohydrates, mention may especially be made of polyhydroxyaldehydes and polyhydroxy ketones of general formula: Cx(H2O)y in which x and y may range from 1 to 1 000 000.

The carbohydrates may be monosaccharides, disaccharides or polysaccharides.

Examples of carbohydrates that may especially be mentioned include amylodextrins, beta-glucans, cyclodextrins, modified corn starch, glycogen, hyaluronic acid, hydroxypropylcyclodextrin, lactose, maltitol, guanosine, glyceryl starch, *Triticum vulgare* starch, trehalose, sucrose and derivatives thereof, raffinose and sodium chondroitin sulfate.

$C_1$-$C_{20}$ alkylene glycols or $C_1$-$C_{20}$ alkylene glycol ethers, alone or used in combination with tri($C_1$-$C_{20}$)alkylsilanes, may also be used as surface-treatment agents.

Examples that may be mentioned include pigments surface-treated with PEG alkyl ether alkoxysilane, for instance pigments treated with PEG-8-methyl ether triethoxysilane sold by Kobo under the name SW pigments.

Silicones such as dimethicones bearing hydrophilic groups, also known under the name dimethicone copolyols or alkyl dimethicone copolyols, may also be suitable for use in the invention as surface treatment agents. In particular, such dimethicones may comprise, as repeating units, $C_1$-$C_{20}$ alkylene oxides, such as ethylene or propylene oxides.

By way of example, mention may be made of the pigment treated with PEG-12-dimethicone, sold by Sensient Corporation under the name LCW AQ Pigment.

The amount of pigments coated with at least one hydrophilic compound and/or of uncoated pigments is especially influenced by the intended use of the cosmetic composition under consideration, and the adjustment of this amount obviously falls within the competence of the composition formulator.

Fillers

The fillers which can be used in the compositions of the invention can be of organic or inorganic nature and especially make it possible to confer on it additional properties of improved stability, wear property, coverage and/or mattness.

The content of filler(s) can range from 2% to 20% by weight, especially from 4% to 12% by weight, relative to the total weight of the said composition.

The fillers used in the compositions according to the present invention can be of lamellar, globular, spherical or fibrous form or of any other form intermediate between these defined forms.

The fillers according to the invention may or may not be surface-coated, and in particular they may be surface-treated with silicones, amino acids, fluorinated derivatives or any other substance which promotes the dispersion and the compatibility of the filler in the composition.

Mention may be made, as examples of inorganic fillers, of clays, talc, mica, silica, hollow silica microspheres, kaolin, calcium carbonate, magnesium carbonate, hydroxyapatite, boron nitride, glass or ceramic microcapsules, composites of silica and of titanium dioxide, such as the TSG series sold by Nippon Sheet Glass, or hydrophobic silica aerogel particles surface-modified by trimethylsilyl groups.

According to a specific form of the invention, the composition of the invention comprises, as filler, at least hydrophobic silica aerogel particles surface-modified by trimethylsilyl groups and/or a lipophilic clay.

As hydrophobic silica aerogels of use in the invention, mention may for example be made of the aerogel sold under the name VM-2260® (INCI name: Silica silylate), by Dow Corning, the particles of which have a mean size of about 1000 microns and a specific surface area per unit of mass ranging from 600 to 800 $m^2$/g.

Mention may also be made of the aerogels sold by Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica silylate), by Dow Corning, the particles of which have a mean size ranging from 5 to 15 microns and a specific surface area per unit of mass ranging from 600 to 800 $m^2$/g.

According to a particular form of the invention, the composition in accordance with the invention comprises at least one lipophilic clay.

The term "lipophilic clay" means any clay that is liposoluble or lipodispersible in the oily phase of the composition.

Clay denotes a material based on hydrated silicates and/or aluminosilicates, of lamellar structure.

The clays can be natural or synthetic and they are rendered lipophilic by treatment with an alkylammonium salt, such as a $C_{10}$ to $C_{22}$ ammonium chloride, for example stearalkonium chloride or distearyldimethylammonium chloride.

They may be chosen from bentonites, in particular bentonites, hectorites and montmorillonites, beidellites, saponites, nontronites, sepiolites, biotites, attapulgites, vermiculites and zeolites.

They are preferably chosen from hectorites and bentonites.

According to one particularly preferred form, use will be made of a lipophilic clay chosen from hydrophobically modified bentonites and hydrophobically modified hectorites, especially a $C_{10}$ to $C_{22}$ quaternary ammonium chloride, such as:

a bentonite modified with stearalkonium chloride, such as the commercial products sold under the name Claytone AF®, Garamite VT®, Tixogel® LG-M, Tixogel® MP 250 Tixogel® VZ and Tixogel® VZ-V XR, by BYK Additives Inc; or the commercial products sold under the name Viscogel® B3, Viscogel® B4, Viscogel® B7, Viscogel® B8, Viscogel® ED, Viscogel® GM, Viscogel® S4 and Viscogel® SD by Bentec S.P.A;

a bentonite modified with stearalkonium chloride in the presence of at least one propylene carbonate and of at least one oil, such as the commercial products Dub Velvet Gum® from Stearinerie Dubois Fils, Myglyol GEL T® from Cremer Oleo, Tixogel® CGT 6030, Tixogel® DBA 6060, Tixogel® FTN, Tixogel® FTN 1564, Tixogel® IPM, Tixogel® LAN, Tixogel® LAN 1563 by BYK Additives Inc;

a hectorite modified with distearyldimethylammonium chloride (INCI name: Disteardimonium Hectorite) such as, for example, that sold under the name Bentone® 38V by Elementis Specialities;

a hectorite modified with distearyldimethylammonium chloride in the presence of at least propylene carbonate or triethyl citrate and of at least one oil, such as the product sold under the name Bentone® GEL DOA V, Bentone® GEL EUG V, Bentone® GEL IHD V, Bentone® GEL ISD V, Bentone® GEL MIO V® Bentone® GEL PTM V® Bentone® SS-71 V, Bentone® VS-5 PC V, Bentone® VS-5 by Elementis Specialities; the commercial products sold under the name Creagel Bentone CPS/Hectone CPS, Creagel Bentone ID/Hectone ID from Creations Couleurs; the commercial products sold under the name NS Gel DM1®, NS Gel PTIS®, NS MGel 1152® from Next Step Laboratories Stop.

The lipophilic clay(s) are present in the composition at concentrations ranging preferably from 0.1 to 5% by weight and more preferentially from 0.1 to 1% by weight relative to the total weight of the composition.

As examples of organic fillers, mention may be made of powders formed of polyamide (Orgasol Nylon® from Atochem), of polyethylene, of poly(methyl methacrylate), of polytetrafluoroethylene powders (Teflon) or of acrylic acid copolymers (Polytrap from Dow Corning), lauroyl lysine, hollow polymeric microspheres, such as those of polyvinylidene chloride/acrylonitrile, such as Expancel (Nobel Industrie), hexamethylene diisocyanate/trimethylol hexyllactone copolymer powder (Plastic Powder from Toshiki), silicone resin microbeads (Tospearl from Toshiba, for example), crosslinked silicone polymer beads coated with silsesquioxane resin (KSP100 from Shin Etsu), synthetic or natural micronized waxes, metal soaps derived from organic carboxylic acids having from 8 to 22 carbon atoms, preferably from 12 to 18 carbon atoms, for example zinc stearate, magnesium stearate, lithium stearate, zinc laurate or magnesium myristate, Polypore® L 200 (Chemdal Corporation) or polyurethane powders, in particular powders formed of crosslinked polyurethane comprising a copolymer, said copolymer comprising trimethylol hexyllactone. It may in particular be a hexamethylene diisocyanate/trimethylol hexyllactone polymer. Such particles are especially commercially available, for example under the name Plastic Powder D-400® or Plastic Powder D-800® from Toshiki, and mixtures thereof.

According to a particular embodiment of the invention, the composition comprises at least one crosslinked elastomeric organopolysiloxane powder coated with silicone resin.

The term "organopolysiloxane elastomer" or "silicone elastomer" means a supple, crosslinked, deformable organopolysiloxane having viscoelastic properties and especially with the consistency of a sponge or a supple sphere. Its modulus of elasticity is such that this material withstands deformation and has a limited ability to extend and to contract. This material is capable of regaining its original shape after stretching.

Such elastomer powders are sold under the names KSP-100®, KSP-101®, KSP-102®, KSP-103®, KSP-104® and KSP-105® by the company Shin-Etsu, and have the INCI name: vinyl dimethicone/methicone silsesquioxane crosspolymer.

Mention may also be made of:
crosslinked elastomeric organopolysiloxane powders coated with silicone resin, such as powders of hybrid silicone functionalized with fluoroalkyl groups, in particular sold under the name KSP-200® by Shin-Etsu and having the INCI name: Trifluoropropyl Dimethicone/Vinyl Trifluoropropyldimethicone/Silsesquioxane Crosspolymer; or
powders of hybrid silicones functionalized with phenyl groups, especially sold under the name KSP-300® by Shin-Etsu and having the INCI name: Diphenyl Dimethicone/Vinyl Diphenyl Dimethicone/Silsesquioxane Crosspolymer.

According to one advantageous embodiment, the compositions according to the invention comprise an organopolysiloxane elastomer powder coated with silsesquioxane resin, having the INCI name Vinyl Dimethicone/Methicone Silsesquioxane Crosspolymer, such as those sold under the names KSP-100®.

The organopolysiloxane elastomer powder(s) coated with a silicone resin may be present at a content ranging from 0.1% to 10% by weight, advantageously from 0.5% to 5% by weight, more particularly from 0.5 to 2% by weight relative to the total weight of said composition.

Water-Soluble or Liposoluble Colorants

A composition according to the invention may also comprise at least one water-soluble colorant and/or a liposoluble colorant, preferably in a proportion of at least 0.01% by weight relative to the total weight of the composition.

For obvious reasons, this amount is liable to vary significantly with regard to the intensity of the desired colour effect and of the colour intensity afforded by the colorants under consideration, and its adjustment clearly falls within the competence of those skilled in the art.

The additional colorants that are suitable for use in the invention may be water-soluble, but may also be liposoluble.

For the purposes of the invention, the term "water-soluble colorant" means any natural or synthetic, generally organic compound, which is soluble in an aqueous phase or water-miscible solvents and which is capable of colouring.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

The water-soluble dyes are, for example, beetroot juice and caramel.

For the purposes of the invention, the term "liposoluble colorant" means any natural or synthetic, generally organic compound, which is soluble in an oily phase or in solvents that are miscible with a fatty substance, and which is capable of imparting colour.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

Applications

According to one embodiment, a composition of the invention may advantageously be in the form of a composition for caring for the skin and/or keratin fibres, the body or the face, in particular the face.

According to another embodiment, a composition of the invention may advantageously be in the form of a composition for making up keratin materials, in particular the skin of the body or of the face, in particular of the face.

Thus, according to a sub-mode of this embodiment, a composition of the invention may advantageously be in the form of a makeup base composition.

A composition of the invention may advantageously be in the form of a foundation.

According to another sub-mode of this embodiment, a composition of the invention may advantageously be in the form of a composition for making up the skin and especially the face. It may thus be an eyeshadow or a face powder.

Such compositions are in particular prepared according to the general knowledge of those skilled in the art.

Throughout the description, including the claims, the term "comprising a" should be understood as being synonymous with "comprising at least one", unless otherwise specified.

The expressions "between . . . and . . . ", "of between . . . and . . . " and "ranging from . . . to . . . " should be understood as meaning limits included, unless otherwise specified.

The invention is illustrated in more detail by the examples and figures presented below. Unless otherwise indicated, the amounts shown are expressed as percentages by weight.

Examples 1 to 4: Foundations in the Form of a Water/Oil Emulsion

| Phase | Ingredients | EX. 1 (invention) | EX. 2 (invention) | EX. 3 (outside the invention) | EX. 4 (outside the invention) |
|---|---|---|---|---|---|
| A1 | POLYGLYCERYL-4 DIISOSTEARATE/POLYHYDROXYSTEARATE SEBACATE (ISOLAN GPS ® from EVONIK) | 0.75 | 0.75 | 0.75 | 0.75 |
|  | PEG-30 DIPOLYHYDROXYSTEARATE (CITHROL DPHS-SO-(MV) from CRODA) | 1.00 | 1.00 | 1.00 | 1.00 |
| A2 | HOMOSALATE | 10 | 10 | 10 | 10 |
|  | ETHYLHEXYL SALICYLATE | 5 | 5 | 5 | 5 |
|  | OCTOCRYLENE | 7 | 7 | 7 | 7 |
| A3 | PDMS 2CST (SILICONE FLUID 2CS ® from DOW CORNING) | 16.00 | 16.00 | 16.00 | 16.00 |
| A4 | DISTEARDIMONIUM HECTORITE (BENTONE V38 ® from ELEMENTIS) | 0.75 | 0.75 | 0.75 | 0.75 |
| A5 | VINYL DIMETHICONE/METHICONE SILSESQUIOXANE CROSSPOLYMER (KSP 100 ® from SHIN ETSU) | 2.00 | 2.00 | 2.00 | 2.00 |
| A6 | VITAMIN E TOCOPHEROL | 1.00 | 1.00 | 1.00 | 1.00 |
| B | Propanediol | 5 | 5 | 5 | 5 |
|  | SCUTELLARIA BAICALENSIS ROOT EXTRACT (BAICALIN 95 MM ® from MMP) | 0.2 | 0.2 | 0.2 | 0.2 |
|  | MAGNESIUM SULFATE | 0.7000 | 0 | 0 | 0.7000 |
|  | CALCIUM CHLORIDE | 0 | 0.7000 | 0 | 0 |
|  | SODIUM CHLORIDE | 0 | 0 | 0.7000 | 0 |
|  | WATER | qs 100 | qs 100 | qs 100 | qs 100 |
|  | PHENOXYETHANOL | 0.50 | 0.50 | 0.50 | 0.50 |
|  | NIACINAMIDE | 2 | 2 | 2 | 2.5 |
|  | CAFFEINE | 1 | 1 | 1 | 0 |
| C | ALCOHOL | 5 | 5 | 5 | 5 |
| D | YELLOW IRON OXIDE COATED WITH ALUMINIUM STEAROYL GLUTAMATE RED IRON OXIDE COATED WITH ALUMINIUM STEAROYL GLUTAMATE BLACK IRON OXIDE COATED WITH ALUMINIUM STEAROYL GLUTAMATE TITANIUM DIOXIDE COATED WITH ALUMINIUM STEAROYL GLUTAMATE | 14 | 14 | 14 | 14 |

Protocol

Preparation of the Aqueous Phase B:

In a glass beaker: the Niaciniamide was dissolved in water with stirring using a magnetic bar, then the caffeine was added in order to obtain a transparent solution, then the baicalin was added in order to obtain a clear yellow transparent solution with a pH of 4.7 and then the salt (MgSO$_4$, CaCl$_2$ or NaCl), propanediol and phenoxyethanol were added in order to obtain a clear yellow transparent solution with a pH of 4.75.

Preparation of the Oily Phase:

In a capsule, a part of the silicone (two times the amount of clay) was taken in order to wet the clay with a flexible spatula. On a hot plate, in the main beaker, the ethylhexyl salicylate was heated with the PEG-30 dipolyhydroxystearate and the polyglyceryl-4 diisostearate/polyhydroxystearate/sebacate to around 55° C., until the PEG-30 dipolyhydroxystearate had melted, and then the mixture was cooled by adding the other two sunscreens (the temperature drops to 30° C.) and the rest of the silicone was added.

Emulsification:

The aqueous phase was added little by little, with stirring on a Moritz stirrer, to the oily phase in order to obtain a concentrated white base, the stirring speed was increased and the mixture was left to stir for 10 minutes until a fluid mixture was obtained. The mixture of modified clay and volatile silicone oil was added to the white base and the resulting mixture was stirred in a turbine very strongly in order to activate the clay, and was left to stir for the 15 minutes until the mixture had thickened. The KSP 100 was added, with stirring on a Moritz stirrer, and the mixture was left for 10 minutes until it had thickened. The vitamin E and then the pigments were added until there was good development of the colour. The formula was then debubbled.

After production, the appearances of all the formulas at room temperature were smooth, homogeneous and fluid. The stability of each of formulas 1 to 4, which are placed in a 30 ml transparent glass mortar for preparing ointment, so that they fill it to ⅔ of its volume, is evaluated:

at room temperature for 2 months;

in an incubator at 4° C. for 2 months;

in an incubator at 45° C. for 2 months.

The results obtained are indicated in the following table:

| Stability measured | EX. 1 (invention) Baicalin Vitamin B3, MgSO$_4$ and caffeine | EX. 2 (invention) Baicalin Vitamin B3, CaCl$_2$ and caffeine | EX. 3 (outside the invention) Baicalin Vitamin B3, NaCl and caffeine | EX. 4 (outside the invention) Baicalin Vitamin B3, MgSO$_4$ without caffeine. |
|---|---|---|---|---|
| Room temperature for 2 months | Stable | Stable | Stable | Stable |
| 4° C. for 2 months | Stable | Stable | Unstable: White smear on surface | Unstable: White smear on surface |
| 45° C. for 2 months | Stable | Stable | Stable | Stable |

Unlike examples 1 and 2 according to the invention, which comprise baicalin, vitamin B3, caffeine and a divalent metal salt, example 3 (with a monovalent metal salt) and example 4 (without caffeine) are unstable at low temperature.

The invention claimed is:

1. A composition for making up and/or caring for keratin materials, in a physiologically acceptable medium, and is, in the form of a water-in-oil emulsion containing at least:
    a) a continuous oily phase,
    b) a discontinuous aqueous phase dispersed in said oily phase;
    c) at least baicalin and/or a derivative thereof and/or a plant extract containing said baicalin and/or derivative thereof;
    d) at least one vitamin B3 and/or a derivative thereof;
    e) at least one of caffeine and a plant extract containing caffeine; and
    f) at least one polyvalent metal cation salt selected from the group consisting of magnesium sulfate and calcium chloride,
    wherein the composition is stable at 4° C., at 25° C. and at 45° C., wherein stable is defined as active agents remaining soluble without crystallization in the aqueous phase, the active agents are the baicalin and/or a derivative thereof and/or a plant extract containing said baicalin and/or a derivative thereof, the vitamin B3 and/or a derivative thereof, and the caffeine and/or a plant extract containing caffeine.

2. The composition according to claim 1, comprising baicalin and/or one of the compounds corresponding to the following formula (I):

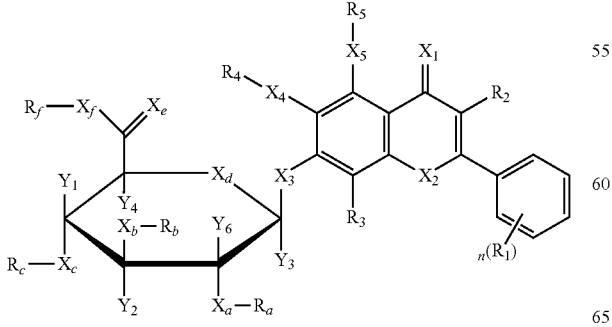

(I)

wherein
each $X_1$, $X_2$, $X_3$, $X_4$, $X_5$, $X_a$, $X_b$, $X_c$, $X_d$, $X_e$ and $X_f$, independently denotes O or S;
each $Y_1$, $Y_2$, $Y_3$, $Y_4$, $Y_6$, independently denotes H or a $(C_1\text{-}C_{10})$alkyl radical;
each $R_4$, $R_5$, $R_a$, $R_b$ et $R_c$, independently denotes H, a $(C_1\text{-}C_{10})$alkyl radical optionally substituted by 1 to 5 groups $R_y$, or a $(C_1\text{-}C_{10})$alkyl-O—$(C_1\text{-}C_{10})$alkyl radical, each $(C_1\text{-}C_{10})$alkyl radical optionally being substituted by 1 to 5 groups $R_y$;
each $R_y$, independently denotes $R_q$ or a $(C_2\text{-}C_{10})$alkenyl, —$(C_2\text{-}C_{10})$alkynyl, —$(C_3\text{-}C_{10})$cycloalkyl, —$(C_8\text{-}C_{14})$bicycloalkyl, —$(C_8\text{-}C_{14})$tricycloalkyl, —$(C_5\text{-}C_{10})$cycloalkenyl, —$(C_8\text{-}C_{14})$tricycloalkenyl, phenyl, naphthyl, —$(C_{14})$aryl radical, each optionally being substituted by one or more radicals $R_z$;
each $R_1$, $R_2$, $R_3$, independently denotes $R_q$ or a —$(C_2\text{-}C_{10})$alkenyl, —$(C_2\text{-}C_{10})$alkynyl, —$(C_3\text{-}C_{10})$cycloalkyl, —$(C_8\text{-}C_{14})$bicycloalkyl, —$(C_8\text{-}C_{14})$tricycloalkyl, —$(C_5\text{-}C_{10})$cycloalkenyl, —$(C_8\text{-}C_{14})$tricycloalkenyl, phenyl, naphthyl, —$(C_{14})$aryl radical, each optionally being substituted by one or more radicals $R_z$;
Rf is H, $(C_1\text{-}C_{12})$ alkyl optionally substituted by 1 to 5 radicals $R_y$, $(C_1\text{-}C_{12})$alkyl-O—$(C_1\text{-}C_{12})$alkyl, each $(C_1\text{-}C_{12})$alkyl radical optionally being substituted by 1 to 5 groups $R_y$;
each $R_q$, independently is CN, OH, halogen, $N_3$, $NO_2$, $N(R_z)_2$, =$NR_z$, CH=$NR_z$, $NR_z$OH, $OR_z$, $COR_z$, C(O)$R_z$, O(CO)O$R_z$, S$R_z$, S(O)$R_z$ or S(O)$_2R_z$;
each $R_z$, independently is —$(C_1\text{-}C_6)$alkyl, —$(C_2\text{-}C_6)$alkenyl, —$(C_3\text{-}C_8)$cycloalkyl, —$(C_3\text{-}C_8)$cycloalkenyl, phenyl, a heterocycle having 3 to 5 branches, CH(halo)$_2$ or C(halo)$_3$; and
n is equal to 0, 1, 2, 3, 4 or 5, and also the salts thereof, the optical isomers thereof, and/or the diastereoisomers thereof.

3. The composition according to claim 1, comprising baicalin corresponding to the following general formula (II):

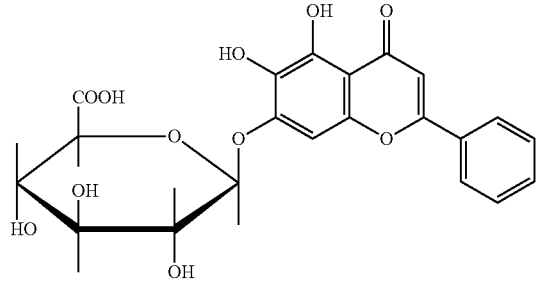

or a plant extract containing same.

4. The composition according to claim 3, wherein the baicalin of formula (II) is present in active material concentrations ranging from 0.01 to 10% by weight relative to the total weight of the composition.

5. The composition according claim 1, wherein the vitamin B3 is niacinamide.

6. The composition according to claim 1, wherein the vitamin B3 and/or one of the derivatives thereof are present in active material concentrations ranging from 0.01 to 20% by weight relative to the total weight of the composition.

7. The composition according to claim 1, wherein the caffeine is present in a content of active material ranging from 0.01 to 10% by weight, relative to the total weight of the composition.

8. The composition according to claim 1, in which the polyvalent metal cation salt(s) are present in a content ranging from 0.01 to 2% by weight, relative to the total weight of the composition.

9. The composition according to claim 1, further comprising one or more emulsifying surfactants.

10. The composition according to claim 1, further comprising at least one additive selected from the group consisting of:
sunscreens,
pigments,
fillers,
additional colorants,
and mixtures thereof.

11. The composition according to claim 1, further comprising at least one pigment.

12. The composition according to claim 1, being in the form of a foundation.

13. A process for making up and/or caring for keratin materials, comprising: application to the keratin materials of a composition according to claim 1.

14. The composition according to claim 3, which comprises a plant extract and the plant extract is a scullcap root extract.

15. The composition according to claim 14, wherein the scullcap root extract is of *Scutellaria baicalensis*, with the INCI name: *SCUTELLARIA BAICALENSIS* ROOT EXTRACT.

16. The composition according to claim 11, wherein the at least one pigment is coated with at least one lipophilic or hydrophobic compound.

17. The composition according to claim 2 or 3, wherein the baicalin of formula (II) or one of the compounds of formula (I) are present in active material concentrations ranging from 0.01 to 10% by weight relative to the total weight of the composition;
wherein the vitamin B3 is niacinamide and is present in active material concentrations ranging from 0.01 to 20% by weight relative to the total weight of the composition;
wherein the caffeine is present in a content of active material ranging from 0.01 to 10% by weight, relative to the total weight of the composition;
wherein the polyvalent metal cation salt(s) are present in a content ranging from 0.01 to 2% by weight, relative to the total weight of the composition; and
wherein the composition is in the form of a foundation.

* * * * *

UNITED STATES PATENT AND TRADEMARK OFFICE
CERTIFICATE OF CORRECTION

PATENT NO. : 11,376,205 B2
APPLICATION NO. : 16/470850
DATED : July 5, 2022
INVENTOR(S) : Hong Li It is certified that error appears in the above-identified patent and that said Letters Patent is hereby corrected as shown below:

In the Claims

In Column 45, Claim 5, Line 5, "according claim 1," should read -- according to claim 1, --.

Signed and Sealed this
Fifteenth Day of November, 2022

Katherine Kelly Vidal
*Director of the United States Patent and Trademark Office*